(12) United States Patent
Muratake et al.

(10) Patent No.: US 8,633,335 B2
(45) Date of Patent: Jan. 21, 2014

(54) RETINOID PRODRUG COMPOUND

(75) Inventors: Hideaki Muratake, Tokyo (JP); Koichi Shudo, Tokyo (JP)

(73) Assignee: Research Founation Itsuu Laboratory, Tokyo (JP)

( * ) Notice: Subject to any disclaimer, the term of this patent is extended or adjusted under 35 U.S.C. 154(b) by 380 days.

(21) Appl. No.: 12/682,966

(22) PCT Filed: Oct. 31, 2007

(86) PCT No.: PCT/JP2007/071184
§ 371 (c)(1),
(2), (4) Date: Jul. 26, 2010

(87) PCT Pub. No.: WO2009/057199
PCT Pub. Date: May 7, 2009

(65) Prior Publication Data
US 2010/0286427 A1 Nov. 11, 2010

(51) Int. Cl.
*C07C 51/367* (2006.01)
(52) U.S. Cl.
USPC .......................................... 562/405
(58) Field of Classification Search
USPC .......................................... 562/405
See application file for complete search history.

(56) References Cited

U.S. PATENT DOCUMENTS 6,326,510 B1  12/2001  Bernardon

FOREIGN PATENT DOCUMENTS

| EP | 1048659 | | 11/2000 |
|---|---|---|---|
| EP | 1048659 A1 | * | 11/2000 |
| JP | 61-022047 | | 1/1986 |
| JP | 61-076440 | | 4/1986 |
| JP | 2-247185 | | 10/1990 |
| JP | 11-507960 | | 7/1999 |
| JP | 2000-500499 | | 1/2000 |
| WO | 97/19052 | | 5/1997 |
| WO | 98/34909 A1 | | 8/1998 |
| WO | 99/24415 | | 5/1999 |
| WO | 00/20358 | | 4/2000 |
| WO | 2005/056516 | | 6/2005 |

OTHER PUBLICATIONS

Toriumi, Y., et al. "Crystallographic studies on retinoidal-active and -inactive aromatic anilides," J.Org.Chem. (1990) 55: 259-263.*
International Search Report issued with respect to PCT/JP2007/071184 (in English), mailed Jan. 15, 2008.
International Preliminary Report on Patentability, including the Written Opinion for PCT/JP2007/071184 (in Japanese and English), mailed May 14, 2010.
Extended European Search Report for European Patent Application No. 07830918.4, mailed Aug. 23, 2011.
Japanese Office Action issued to with respect to Japanese Office Action 2006-275097, dated Jul. 31, 2012 with partial English translation.
Official Action issued with respect to patent family member European Patent App. No. 07830918.4, dated Aug. 1, 2012.

* cited by examiner

*Primary Examiner* — Johann R Richter
*Assistant Examiner* — Kofi Adzamli
(74) *Attorney, Agent, or Firm* — Greenblum & Bernstein, P.L.C.

(57) ABSTRACT

A compound represented by the following general formula (I):

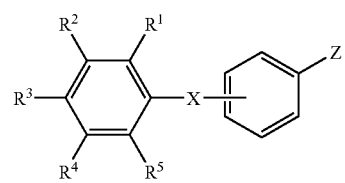

[$R^1$ to $R^5$ represent hydrogen atom, an alkyl group, or a trialkylsilyl group, X represents —NH—CO—, —CO—NH—, —N(COR$^6$)—CO—, —CO—N(COR$^7$)— ($R^6$ and $R^7$ represent a lower alkoxy group, or a carboxy-substituted phenyl group) etc.; and Z represents —Y—CH(R$^{12}$)—COOH, —CHO, —CH═CH—COOH, or —COOR$^{13}$ (Y represents a single bond, —CH$_2$—, —CH(OH)—, —CO—, —CO—NH—, or —CO—NH—CH$_2$—CO—NH—, $R^{12}$ represents hydrogen atom or a lower alkyl group, and $R^{13}$ represents hydrogen atom, —CH(R$^{14}$)—COOH($R^{14}$ represents hydrogen atom, a lower alkyl group, or hydroxy group), —[CH$_2$CH$_2$—O]$_n$—CH$_2$—CH$_2$—OH, —CH$_2$—O—[CH$_2$CH$_2$—O]$_m$—CH$_2$—OH, or —[CH(CH$_3$)—CO—O]$_p$—CH(CH$_3$)—COOH (m, n and p represent an integer of 1 to 100))], a salt thereof or an ester thereof, which has a property of being converted into a retinoid after absorption in vivo.

7 Claims, No Drawings

RETINOID PRODRUG COMPOUND

TECHNICAL FIELD

The present invention relates to a retinoid prodrug compound which exhibits the same physiological activities as those of retinoids such as retinoic acid in living bodies.

BACKGROUND ART

Retinoic acid (vitamin A acid), an active metabolite of vitamin A, has extremely important physiological functions, e.g., inducing differentiation of immature cells under development processes toward mature cells having specific functions, enhancement of cell proliferation, life support action, and the like. It has also been revealed that various vitamin A derivatives synthesized so far also have similar physiological functions, for example, the benzoic acid derivatives disclosed in Japanese Patent Unexamined Publication (KOKAI) Nos. 61-22047 and 61-76440, the compounds described in Journal of Medicinal Chemistry, 1988, Vol. 31, No. 11, p. 2182, and the like. Retinoic acid and compounds having retinoic acid-like biological activities are collectively referred to as "retinoids".

For example, it was proved that all-trans retinoic acid binds as a ligand to the retinoic acid receptor (RAR) present in cellular nucleus, which belongs to the intranuclear receptor super family (Evans, R. M., Science, 240, p. 889, 1988), and regulates proliferation and differentiation of animal cells or cellular mortalities (Petkovich, M., et al., Nature, 330, pp. 444-450, 1987). In addition, as for expression of physiological activities of retinoic acid, the existence of retinoid X receptor (RXR, of which ligand is 9-cis-retinoic acid) has been elucidated. The retinoid X receptor has been revealed to control the expression of the activities of retinoic acid by forming a dimer with the retinoic acid receptor (RAR) to induce or suppress transcription of a target gene (Mangelsdorf, D. J. et al., Nature, 345, pp. 224-229).

It has also been suggested that the aforementioned compounds having the retinoic acid-like biological activities (e.g., 4-[(5,6,7,8-tetrahydro-5,5,8,8-tetramethyl-2-naphthalenyl)carbamoyl]benzoic acid (Am80), etc.) also bind to RAR in similar manners to that of retinoic acid to exhibit their physiological actions (see, Hashimoto, Y., Cell Struct. Funct., 16, pp. 113-123, 1991; Hashimoto, Y., et al., Biochem. Biophys. Res. Commun., 166, pp. 1300-1307, 1990). These compounds were found to be clinically useful for therapeutic and preventive treatments of vitamin A deficiency disease, hyperkeratosis of epithelial tissue, rheumatism, delayed allergy, bone diseases, leukemia and certain types of cancer. For example, Am80 is clinically used as a therapeutic agent for recurrent leukaemia, and 4-[3,5-bis-(trimethylsilyl)benzamido]benzoic acid (Am555S, Japanese Patent Unexamined Publication No. 2-247185, etc.) is under the clinical development in the United States as an orally administrable antitumor agent.

As described above, retinoids are used as therapeutic agents for cancers, dermatological agents, and the like, and also have significant possibility as therapeutic agents for other various intractable diseases. However, the currently used retinoids are not fully satisfactory from viewpoints of side reactions and the like, and improvements have been desired in enhancement of selectivity for target organ and reduction of organopathy induced by acidic groups, as well as relief of direct actions on the alimentary canal especially in the case of oral administration, and the like. The latter problem may possibly be solved by providing a retinoid prodrug compound having a property of being converted into a retinoid after absorption in vivo. However, almost no compounds have been proposed so far from the above viewpoint.

Patent document 1: Japanese Patent Unexamined Publication No. 61-22047
Patent document 2: Japanese Patent Unexamined Publication No. 61-76440
Patent document 3: Japanese Patent Unexamined Publication No. 2-247185
Non-patent document 1: Journal of Medicinal Chemistry, 31, No. 11, p. 2182, 1988
Non-patent document 2: Cell struct. Funct., 16, pp. 113-123, 1991
Non-patent document 3: Biochem. Biophys. Res. Commun., 166, pp. 1300-1307, 1990

DISCLOSURE OF THE INVENTION

Object to be Achieved by the Invention

An object of the present invention is to provide a retinoid prodrug compound having a property of being converted into a retinoid after absorption in a living body. More specifically, the object of the present invention is to provide a retinoid prodrug compound which, per se, has substantially no retinoid action, or has weak retinoid action, but is converted into a potent retinoid by an enzymatic chemical modification after absorption in a living body.

Means for Achieving the Object

The inventors of the present invention conducted various studies to achieve the aforementioned object, and as a result, found that the compounds represented by the following general formula were very useful as retinoid prodrug compounds, and accomplished the present invention.

The present invention thus provides a compound represented by the following general formula (I):

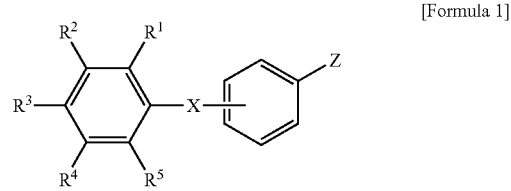

[Formula 1]

[wherein $R^1$, $R^2$, $R^3$, $R^4$ and $R^5$ independently represent hydrogen atom, a lower alkyl group, or a tri(lower alkyl)silyl group, where two adjacent lower alkyl groups represented by them may bond together to form a 5- or 6-membered ring which may have one or two or more alkyl groups together with the carbon atoms in the benzene ring to which they bond; X represents —NH—CO—, —CO—NH—, —N(COR$^6$)—CO—, —CO—N(COR$^7$)—, —CO—N[CON(R$^8$)(R$^9$)]—, or —N[CON(R$^{10}$)(R$^{11}$)] (R$^6$ and R$^7$ represent a lower alkoxy group (this alkoxy group may have a substituent) or a phenyl group (this phenyl group has at least one alkoxycarbonyl group or carboxy group as a substituent, and may also have another substituent), and $R^8$, $R^9$, $R^{10}$ and $R^{11}$ independently represent hydrogen atom or a lower alkyl group); and Z represents —Y—CH(R$^{12}$)—COOH, —CHO, —CH=CH—COOH, or —COOR$^{13}$ (Y represents a single bond, —CH$_2$—, —CH(OH)—, —CO—, —CO—NH—, or —CO—NH—CH$_2$—CO—NH—, R$^{12}$ represents hydrogen atom or a lower alkyl group, and $R^{13}$ represents hydrogen atom, —CH($R^{14}$)—COOH($R^{14}$ represents hydrogen atom, a lower alkyl group, or hydroxy group), —[CH$_2$CH$_2$—O]$_n$—CH$_2$—CH$_2$-OH (n represents an integer of 1 to 100), —CH$_2$-O—[CH$_2$CH$_2$—O]$_m$—CH$_2$-OH (m represents an integer of 1 to 100), or —[CH(CH$_3$)—CO—O]$_p$—CH(CH$_3$)—COOH (p represents an integer of 1 to 100), provided that when X is —NH—CO— or —CO—NH—, $R^{13}$ represents a group other than hydrogen atom)], or a salt thereof.

According to preferred embodiments of the aforementioned invention, there are provided the aforementioned compound or a salt thereof, wherein X and Z are at para-positions with respect to each other; the aforementioned compound or a salt thereof, wherein $R^1$, $R^4$ and $R^5$ are hydrogen atoms, and $R^2$ and $R^3$ are lower alkyl groups; the aforementioned compound or a salt thereof, wherein $R^1$, $R^4$ and $R^5$ are hydrogen atoms, and $R^2$ and $R^3$ bond to each other to form a 6-membered ring; the aforementioned compound or a salt thereof, wherein $R^1$, $R^4$ and $R^5$ are hydrogen atoms, and $R^2$ and $R^3$ bond to each other to form 5,5,8,8-tetramethyl-5,6,7,8-tetrahydronaphthalene ring; and the aforementioned compound or a salt thereof, wherein $R^1$, $R^3$ and $R^5$ are hydrogen atoms, and $R^2$ and $R^4$ are trimethylsilyl groups.

According to further preferred embodiments, there are provided the aforementioned compound or a salt thereof, wherein X is —N(COR$^6$)—CO— or —CO—N(COR$^7$)— ($R^6$ and $R^7$ represent methoxy group or ethoxy group, or a phenyl group substituted with carboxyl group), and Z is —COOR$^{13}$ ($R^{13}$ is hydrogen atom); and the aforementioned compound or a salt thereof, wherein X is —NH—CO— (the carbon atom of this amido group bonds to the benzene ring on which Z substitutes), and Z is —Y—CH($R^{12}$)—COOH (Y is —CH$_2$—, —CH(OH)— or —CO—) or —COOR$^{13}$.

From another aspect, there is provided a medicament comprising a compound represented by the aforementioned general formula or a physiologically acceptable salt thereof as an active ingredient. This medicament is useful as an agent having retinoid-like actions. There is further provided use of the aforementioned compound or a salt thereof for manufacture of the aforementioned medicament.

BEST MODE FOR CARRYING OUT THE INVENTION

In the aforementioned the general formula (I), $R^1$, $R^2$, $R^3$, $R^4$ and $R^5$ independently represent hydrogen atom, a lower alkyl group, or a tri(lower alkyl)silyl group. As the lower alkyl group, a linear or branched alkyl group having about 1 to 6 carbon atoms, preferably 1 to 4 carbon atoms, can be used. For example, methyl group, ethyl group, n-propyl group, isopropyl group, n-butyl group, sec-butyl group, tert-butyl group, and the like can be used. The same shall apply to other lower alkyl groups referred to in this specification, and the same shall also apply to alkyl moieties of substituents having an alkyl moiety (e.g., alkoxy group). As the tri(lower alkyl) silyl group, for example, trimethylsilyl group is preferred. For example, it is preferred that $R^1$, $R^4$ and $R^5$ are hydrogen atoms, and $R^2$ and $R^3$ are lower alkyl groups. It is also preferred that $R^1$, $R^3$ and $R^5$ are hydrogen atoms, and $R^2$ and $R^4$ are tri(lower alkyl)silyl groups, and it is more preferred that $R^1$, $R^3$ and $R^5$ are hydrogen atoms, and $R^2$ and $R^4$ are trimethylsilyl groups.

Adjacent two lower alkyl groups selected from the group consisting of those represented by $R^1$, $R^2$, $R^3$, $R^4$ and $R^5$ may bond to together to form one or two, preferably one, 5- or 6-membered ring which may have one or two or more alkyl groups together with the carbon atoms in the benzene ring to which they bond. As the alkyl group substitutable on the ring, a linear or branched alkyl group having about 1 to 6 carbon atoms, preferably 1 to 4 carbon atoms, can be used. For example, methyl group, ethyl group, and the like can be used, and preferably 2 to 4 methyl groups, more preferably 4 methyl groups, may substitute. For example, it is preferred that the benzene ring on which $R^2$ and $R^3$ substitute, $R^2$ and $R^3$ form 5,6,7,8-tetrahydronaphthalene ring, 5,5,8,8-tetramethyl-5,6,7,8-tetrahydronaphthalene ring, or the like.

X represents —NH—CO—, —CO—NH—, —N(COR$^6$)—CO—, —CO—N(COR$^7$)—, —CO—N[CON($R^8$)($R^9$)]—, or —N[CON($R^{10}$)($R^{11}$)], $R^6$ and $R^7$ represent a lower alkoxy group which may have a substituent, or a phenyl group (this phenyl group has at least one alkoxycarbonyl group or carboxy group as a substituent, and may also have another substituent), and $R^8$, $R^9$, $R^{19}$ and $R^{11}$ independently represent hydrogen atom or a lower alkyl group. It is preferred that X and Z are at the para-positions with respect to each other on the benzene ring to which they bind. As X, —NH—CO— (the carbon atom of this amido group binds to the benzene ring on which Z substitutes) is preferred. When X represents —N(COR$^6$)—CO—, —CO—N(COR$^7$)—, —CO—N[CON($R^8$)($R^9$)]—, or —N[CON($R^{10}$)($R^{11}$)], it is preferred that Z is —COOH. When X is —NH—CO— (the carbon atom of this amido group bonds to the benzene ring on which Z substitutes), it is preferred that Z is —Y—CH($R^{12}$)—COOH (it is preferred that Y is —CH$_2$—, —CH(OH)—, or —CO—, and it is more preferred that Y is —CH$_2$—) or —COOR$^{13}$ ($R^{13}$ is a group other than hydrogen atom). The symbols m, n, and p each represent an integer of 1 to 100, and they may be in the range of about 5 to 50, more preferably about 5 to 30.

The aforementioned compound may form a base addition salt, and it may exist as a metal salt such as, for example, sodium salt, potassium salt, magnesium salt, or calcium salt, an ammonium salt, an organic amine salt such as triethylamine salt or ethanolamine salt, or the like. Among such salts, physiologically acceptable salts can be used as an active ingredient of the medicament of the present invention. Further, in the aforementioned compound, the carboxyl group existing in the Z moiety may form an ester. The ester referred to in the expression "a compound, a salt thereof or an ester thereof" used in this specification means an ester formed by the carboxyl group existing in the Z moiety.

As the aforementioned ester, a physiologically acceptable ester is preferred. Specific examples of preferred residues forming the ester include, for example, methyl group, ethyl group, propyl group, isopropyl group, butyl group, isobutyl group, t-butyl group, benzyl group, acetoxymethyl group, 1-(acetoxy)ethyl group, propionyloxymethyl group, 1-(propionyloxy)ethyl group, butyryloxymethyl group, 1-(butyryloxy)ethyl group, isobutyryloxymethyl group, 1-(isobutyryloxy)ethyl group, valeryloxymethyl group, 1-(valeryloxy) ethyl group, isovaleryloxymethyl group, 1-(isovaleryloxy) ethyl group, pivaloyloxymethyl group, 1-(pivaloyloxy)ethyl group, methoxycarbonyloxymethyl group, 1-(methoxycarbonyloxy)ethyl group, ethoxycarbonyloxymethyl group, 1-(ethoxycarbonyloxy)ethyl group, propoxycarbonyloxymethyl group, 1-(propoxycarbonyloxy)ethyl group, isopropoxycarbonyloxymethyl group, 1-(isopropoxycarbonyloxy) ethyl group, buthoxycarbonyloxymethyl group, 1-(buthoxycarbonyloxy)ethyl group, isobuthoxycarbonyloxymethyl group, 1-(isobuthoxycarbonyloxy)ethyl group, t-buthoxycarbonyloxymethyl group, 1-(t-buthoxycarbonyloxy)ethyl group, cyclopentanecarbonyloxymethyl group, 1-(cyclopentanecarbonyloxy)ethyl group, cyclohexanecarbonyloxymethyl group, 1-(cyclohexanecarbonyloxy)ethyl group, cyclopentyloxycarbonyloxymethyl group, 1-(cyclopentyloxycarbonyloxy)ethyl group, cyclohexyloxycarbonyloxymethyl group, 1-(cyclohexyloxycarbonyloxy)ethyl group, benzolyoxymethyl group, 1-(benzolyoxy)ethyl group, phenoxycarbonyloxymethyl group, 1-(phenoxycarbonyloxy)ethyl group, (5-methyl-2-oxo-1,3-dioxolen-4-yl)methyl group, 2-trimethylsilylethyl group, and the like, but the examples are not limited to these.

The compounds of the present invention may have one or two or more asymmetric carbon atoms depending on types of substituents. Arbitrary optical isomers based on these asymmetric carbon atoms, arbitrary mixtures of optical isomers, racemates, diastereomers based on two or more asymmetric carbon atoms, arbitrary mixtures of diastereomers, and the like all fall within the scope of the present invention. Further, arbitrary hydrates or solvates of the compounds in free form or in the form of a salt also fall within the scope of the present invention.

Preferred compounds among the compounds of the present invention include the following compounds. However, the compounds of the present invention or compounds usable as an active ingredient of the medicament of the present invention are not limited to the following compounds. In the exemplary compounds, Me represents methyl group, Et represents ethyl group, and n represents an integer of, for example, about 12 (when PEG having a molecular weight of 600 is used, n is about 12.2).

[Formula 2]

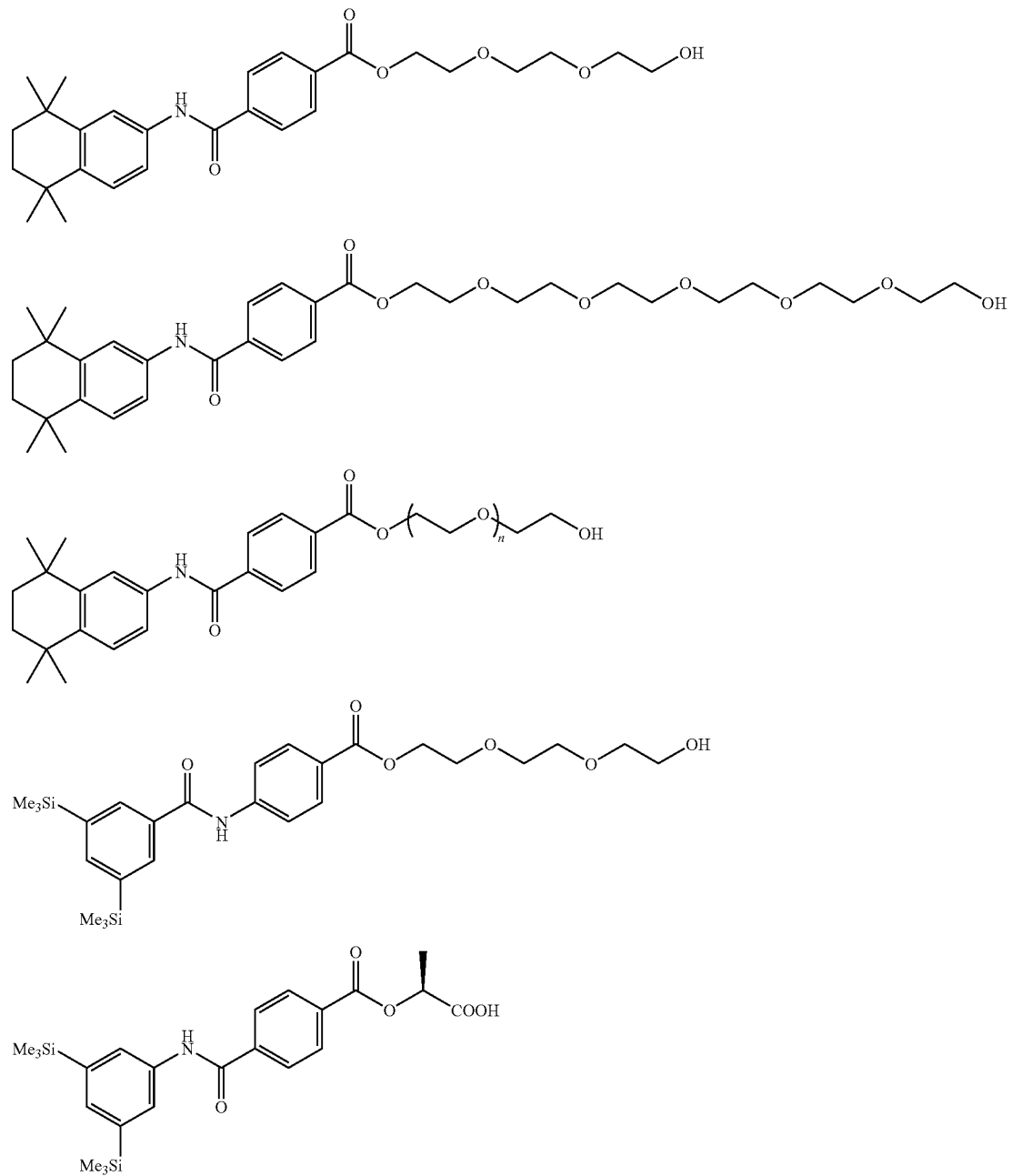

-continued
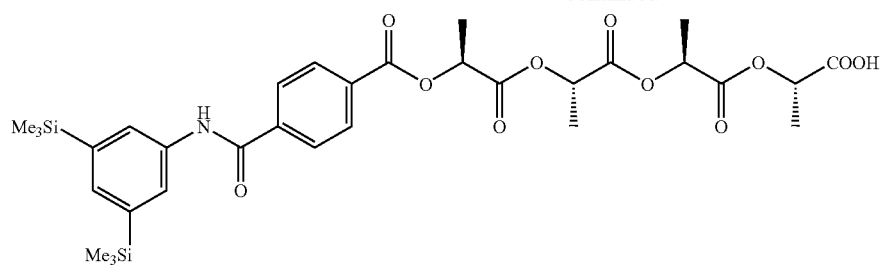
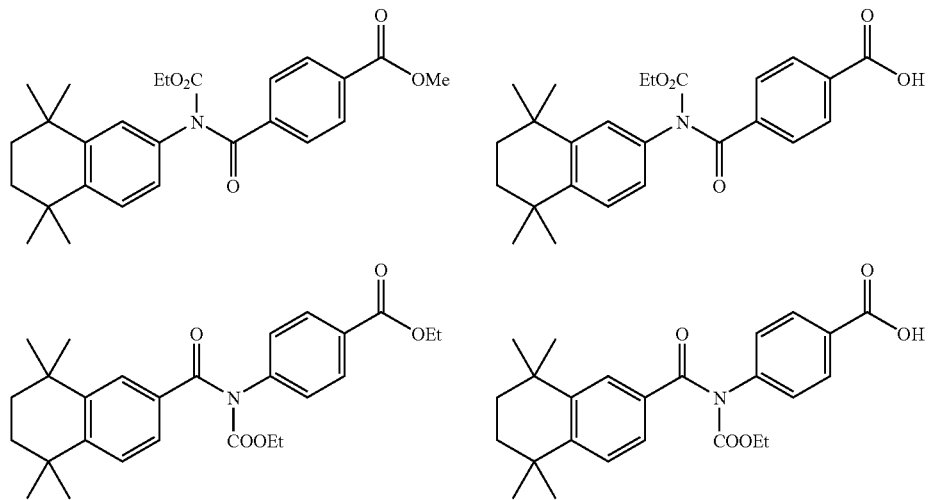
[Formula 3]
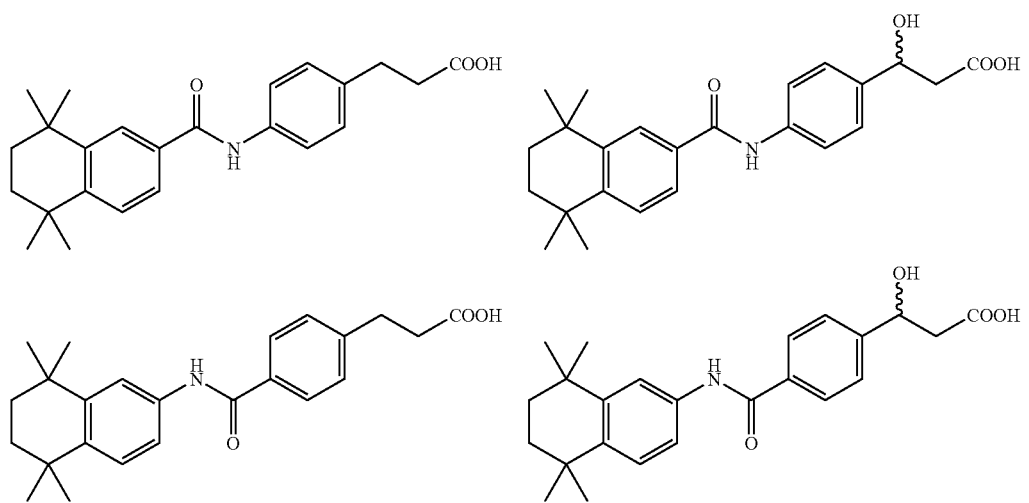

-continued
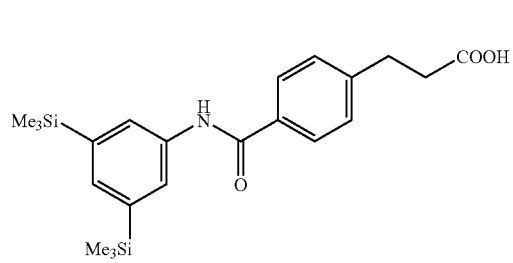
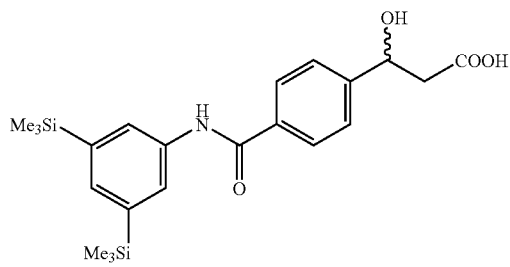
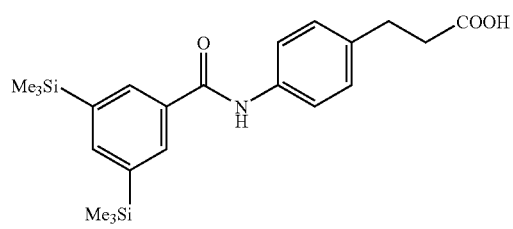
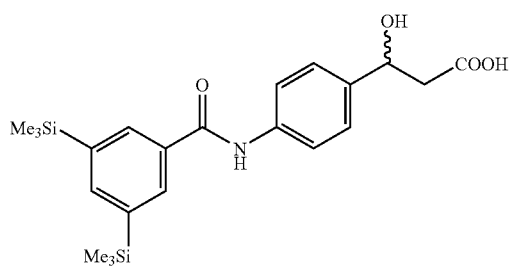
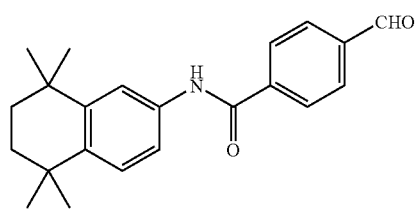
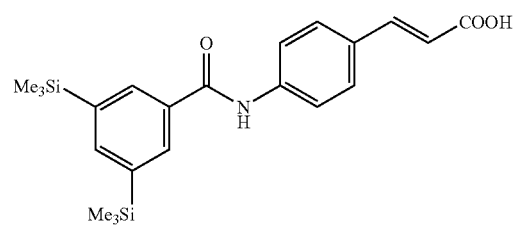
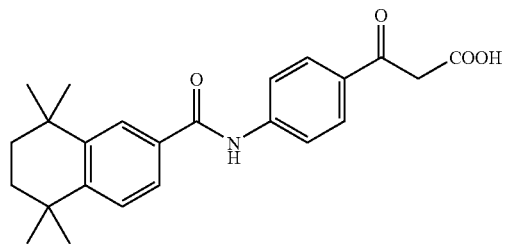
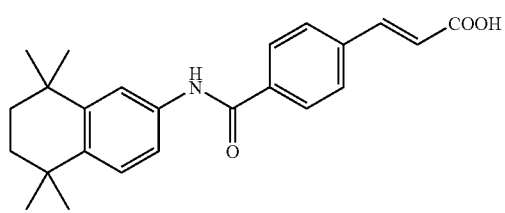
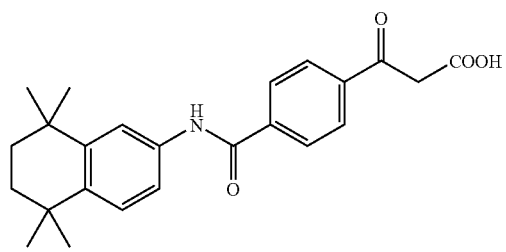
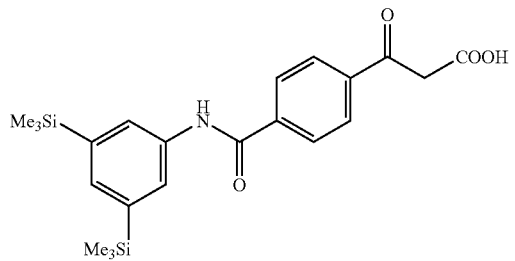
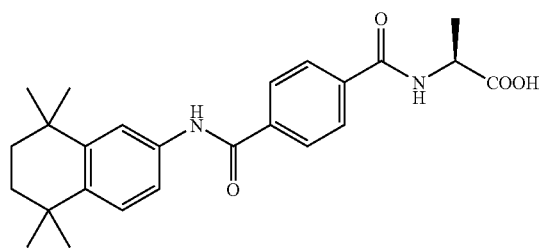
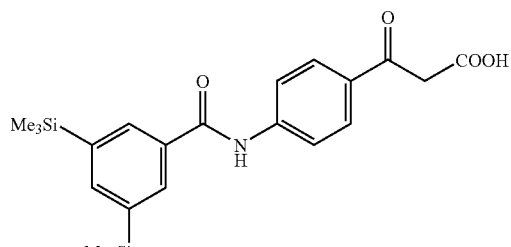

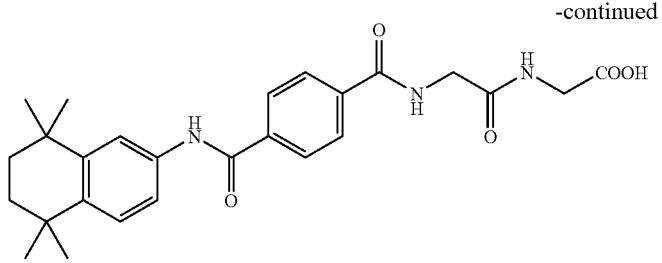

As for the preparation methods of the compounds represented by the aforementioned general formula (I), synthesis examples of typical compounds falling within the aforementioned compounds are specifically described in detail in the examples given in the present specification. Further, as for modification of the benzene ring on which $R^1$, $R^2$, $R^3$, $R^4$ and $R^5$ substitute, for example, known literatures describing the preparation methods of Am80 or Am555S can be referred to. Therefore, those skilled in the art can easily prepare any compounds falling within the scope of the aforementioned general formula (I) by referring to these examples and known literatures, and if necessary, appropriately modifying or altering the preparation methods.

The compounds represented by the aforementioned general formula (I) are compounds which, per se, have substantially no physiological action as retinoid, or has weak retinoid action, but is converted into a potent retinoid by an enzymatic chemical modification after absorption in vivo, and binds to a retinoid receptor to exhibit retinoid-like actions. The term "retinoid receptor" used in this specification includes the retinoic acid receptors RAR and RXR, and means one or two or more kinds of receptors with which retinoids such as retinoic acid can interact. The aforementioned compounds are useful as prodrugs of retinoid, and medicaments containing the aforementioned compounds as an active ingredient are useful as agents having retinoid actions. Although it is not intended to be bound by any specific theory, in order for the compounds of the present invention represented by the general formula (I) to exhibit retinoid-like actions, the compounds of the aforementioned general formula (I) must be metabolized into compounds where Z is carboxyl group, and these compounds having carboxyl group serve as active metabolites and exhibit retinoid-like actions. The aforementioned active metabolites with the retinoid-like actions have, for example, cell differentiating action, cell proliferation enhancing action, life supporting action, and the like, and exhibit prophylactic and/or therapeutic action on vitamin A deficiency disease, karatosis of the epithelial tissue, psoriasis, allergic disease, immunological disease such as rheumatism, bone disease, leukemia, or cancer.

The medicament containing the compound represented by the aforementioned general formula (I) as a retinoid prodrug compound comprises, as an active ingredient, one or two or more kinds of substances selected from the group consisting of the compounds represented by the aforementioned general formula (I), salts thereof, and hydrates and solvates thereof. As the medicament of the present invention, the aforementioned substance, per se, may be administered. However, a pharmaceutical composition for oral administration or parenteral administration may preferably be administered which can be prepared by a method well known to those skilled in the art. Examples of the pharmaceutical compositions suitable for oral administrations include, for example, tablets, capsules, powders, subtilized granules, granules, liquids, syrups and the like. Examples of the pharmaceutical compositions suitable for parenteral administrations include, for example, injections, suppositories, inhalants, eye drops, nasal drops, and the like.

The aforementioned pharmaceutical composition can be prepared by adding pharmacologically and pharmaceutically acceptable additives. Examples of pharmacologically and pharmaceutically acceptable additives include, for example, excipients, disintegrators and disintegrating aids, binders, lubricants, coating agents, colorants, diluents, base materials, dissolving agents and dissolving aids, isotonic agents, pH modifiers, stabilizers, propellants, adhesives and the like.

Dose of the medicament of the present invention is not particularly limited, and can be suitably selected depending on type or level of action of the medicament, and changed depending on various factors that should usually be taken into consideration, such as weight and age of patients, type and symptoms of a disease, and route of administration. The dose can generally be selected by referring to the dose of retinoic acid or the like used as a medicament and by considering absorption efficiency and metabolic efficiency of the prodrug. For example, in the case of oral administration, it can be used in the range of about 0.01 to 1,000 mg per day for adults.

EXAMPLES

The present invention will be more specifically explained with reference to examples. However, the scope of the present invention is not limited to the following examples.

Example 1

2-[2-(2-Hydroxy)ethoxy]ethyl 4-[(5,6,7,8-tetrahydro-5,5,8,8-tetramethyl-2-naphthyl)carbamoyl]benzoate

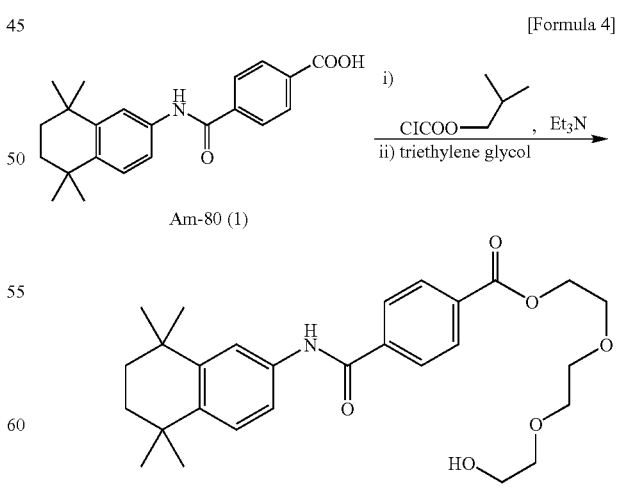

An ice-cooled solution of Am-80 (1, 40 mg, 0.114 mmol) and triethylamine (48 µl, 0.345 mmol) in dichloromethane (2.5 ml) was added with isobutyl chloroformate (16 μl, 0.123 mmol), and the mixture was stirred for 1 hour. This reaction mixture was added with triethylene glycol (152 μl, 1.14 mmol), and the mixture was further stirred at room temperature for 16 hours. The reaction mixture was added with saturated aqueous sodium hydrogencarbonate, and the mixture was extracted with ethyl acetate. The organic layer was washed with water, and dried over anhydrous sodium sulfate, then the solvent was evaporated, and the residue was purified by silica gel column chromatography (eluted with 7 to 10% methanol-chloroform) to obtain 44 mg (80%) of the title compound 2.

Colorless fine needles, melting point: 123.5-124.5° C. (dichloromethane-hexane)

MS (m/z): 483 ($M^+$, 15), 468 (21), 378 (4), 318 (13), 291 (7), 149 (15), 104 (16), 89 (9), 75 (8), 58 (8), 45 (100), 31 (14)

IR (KBr) $cm^{-1}$: 1711, 1646

$^1$H-NMR (CDCl$_3$) δ: 1.28 (6H, s), 1.30 (6H, s), 1.69 (4H, s), 2.48 (1H, br s, OH), 3.58-3.64 (2H, m), 3.66-3.75 (6H, m), 3.84-3.89 (2H, m), 4.50-4.55 (2H, m), 7.31 (1H, d, J=8.5 Hz), 7.45 (1H, dd, J=8.5, 2.5 Hz), 7.55 (1H, d, J=2.5 Hz), 7.92 (2H, $A_2B_2$, J=8 Hz), 7.94 (1H, br s, CONH), 8.15 (2H, $A_2B_2$, J=8 Hz)

Example 2

Hexaethylene Glycol Ester of Am-80

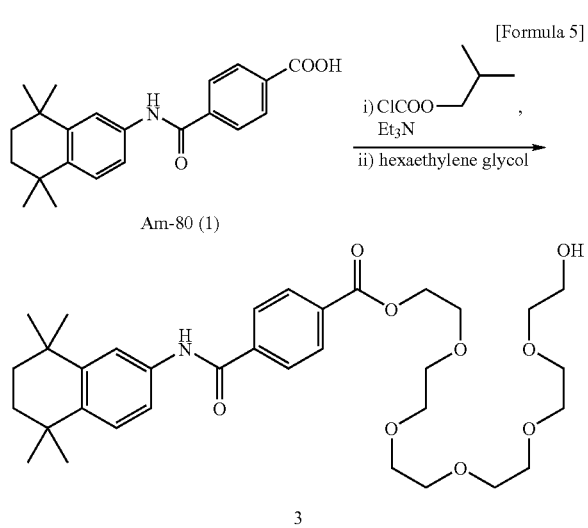

[Formula 5]

3

In the same manner as that mentioned above, the title compound 3 (49 mg, 70%) was obtained from Am-80 (1, 40 mg, 0.114 mmol) and hexaethylene glycol (322 mg, 1.14 mmol).

Colorless vitreous substance

MS (m/z): 615 ($M^+$, 5), 600 (2), 378 (3), 362 (3), 334 (3), 318 (3), 291 (4), 193 (3), 149 (4), 133 (4), 104 (7), 89 (21), 45 (100)

IR (CHCl$_3$) $cm^{-1}$: 1713, 1669

$^1$H-NMR (CDCl$_3$) δ: 1.28 (6H, s), 1.30 (6H, s), 1.69 (4H, s), 2.28 (1H, br s, OH), 3.55-3.74 (20H, m), 3.82-3.88 (2H, m), 4.47-4.53 (2H, m), 7.30 (1H, d, J=8.5 Hz), 7.46 (1H, dd, J=8.5, 2.5 Hz), 7.57 (1H, d, J=2.5 Hz), 7.94 (2H, $A_2B_2$, J=8 Hz), 8.14 (2H, $A_2B_2$, J=8 Hz), 8.20 (1H, br s, CONH)

Example 3

Polyethylene Glycol (Average Molecular Weight: 600) Ester of Am-80

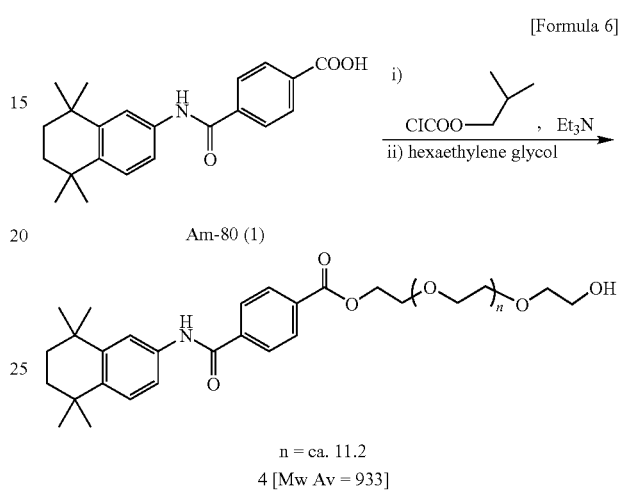

[Formula 6]

n = ca. 11.2

4 [Mw Av = 933]

In the same manner as that mentioned above, the title compound 4 (132 mg, about 83%) was obtained from Am-80 (1, 60 mg, 0.171 mmol) and polyethylene glycol (1.026 g, about 1.71 mmol).

Colorless candy-like substance

MS (mHz): 703 (corresponding to octaethylene derivative, 0.3), 672 (0.3), 615 (0.3), 351 (24), 336 (100), 149 (68), 121 (23), 104 (21), 65 (28), 45 (33)

IR (CHCl$_3$) $cm^{-1}$: 1713, 1668

$^1$H-NMR (CDCl$_3$) δ: 1.27 (6H, s), 1.28 (6H, s), 1.68 (4H, s), 3.00 (1H, br s, OH), 3.55-3.73 (ca. 45H, m), 3.81-3.87 (2H, m), 4.46-4.52 (2H, m), 7.28 (1H, d, J=8.5 Hz), 7.51 (1H, dd, J=8.5, 2 Hz), 7.62 (1H, d, J=2 Hz), 8.01 (2H, $A_2B_2$, J=8 Hz), 8.10 (2H, $A_2B_2$, J=8 Hz), 8.74 (1H, br s, CONH)

Example 4

(S)-1-(Benzyloxycarbonyl)ethyl 4-[[3,5-di(trimethylsilyl)phenyl]carbamoyl]benzoate

[Formula 7]

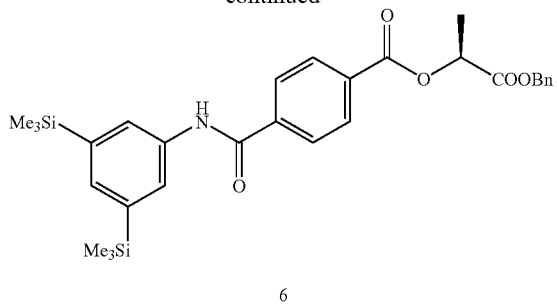

6

A solution of Am-55S (3, 60 mg, 0.156 mmol) and benzyl L-lactate (31 mg, 0.172 mmol) in dichloromethane (3 ml) was added with dicyclohexylcarbodiimide (39 mg, 0.189 mmol) and 4-dimethylaminopyridine (2 mg, 16.4 μmol), and the mixture was stirred at room temperature for 5 hours. The reaction mixture was added with saturated aqueous sodium hydrogencarbonate, and the mixture was extracted with ethyl acetate. The organic layer was washed with water, and dried over anhydrous sodium sulfate, and then the solvent was evaporated. The residue was purified by silica gel column chromatography (eluted with chloroform) to obtain 56 mg (66%) of the title compound 4.

Colorless candy-like substance
MS (m/z): 547 ($M^+$, 18), 368 (4), 311 (5), 104 (6), 91 (100), 73 (11)
IR ($CHCl_3$) $cm^{-1}$: 1721, 1671
$^1$H-NMR ($CDCl_3$) δ: 0.29 (18H, s), 1.65 (3H, d, J=7 Hz), 5.17 (1H, d, J=12.5 Hz), 5.23 (1H, d, J=12.5 Hz), 7.30-7.37 (5H, m), 7.46 (1H, t, J=0.5 Hz), 7.80 (2H, br s), 7.93 (2H, $A_2B_2$, J=8.5 Hz), 8.13 (2H, $A_2\underline{B}_2$, J=8.5 Hz), 8.13 (1H, br s, $\overline{C}$ONH)

Example 5

(S)-1-(Carboxyl)ethyl 4-[[3,5-di(trimethylsilyl)phenyl]carbamoyl]benzoate

[Formula 8]

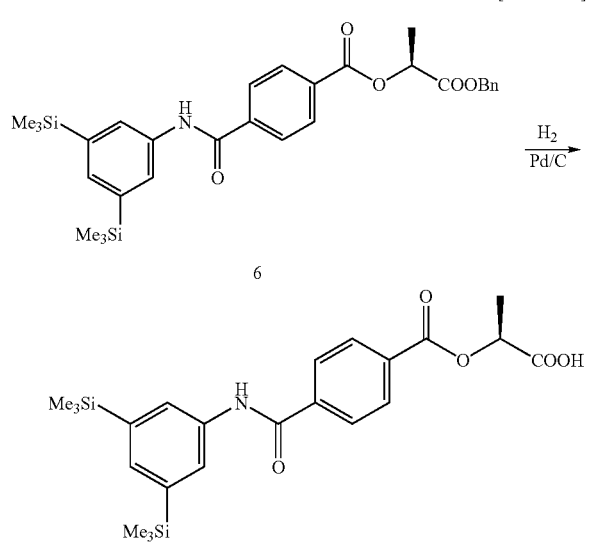

A suspension of the compound 6 (54 mg, 98.7 μmol) obtained above and palladium-carbon (10%, 6 mg) in methanol (4 ml) was subjected to catalytic reduction for 30 minutes under a hydrogen atmosphere of atmospheric pressure. The reaction mixture was filtered through Cerite, and Cerite was washed with 10% methanol-chloroform. The solvent was evaporated, and then the resulting crystals were recrystallized to obtain the title compound 7 (38 mg, 84%).

Colorless scales, melting point: 198-200° C. (dichloromethane-hexane)
MS (m/z): 457 ($M^+$, 89), 370 (93), 221 (33), 176 (39), 149 (60), 129 (29), 104 (35), 75 (29), 73 (100)
IR ($CHCl_3$) $cm^{-1}$: 1720, 1709, 1644, 1626
$^1$H-NMR ($CDCl_3$) δ: 0.30 (18H, s), 1.72 (3H, d, J=7 Hz), 5.42 (1H, q, J=7 Hz), 7.46 (1H, br s), 7.77 (2H, br s), 7.80 (1H, br s, CONH), 7.97 (2H, $A_2B_2$, J=8.5 Hz), 8.21 (2H, $A_2\underline{B}_2$, J=8.5 Hz)

Example 6

(S)—O-tert-Butyllactic acid benzyl ester

[Formula 9]

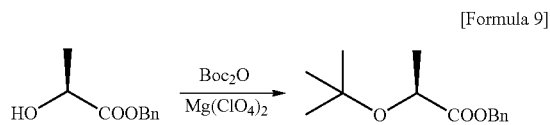

A solution of O-lactic acid benzyl ester (18.0 g, 0.100 mol) and di-t-butyl dicarbonate (54.5 g, 0.250 mol) in dichloromethane (100 ml) was added with magnesium perchlorate (2.23 g, 10 mmol), and the mixture was refluxed by heating for 24 hours. The reaction mixture was left to cool, and then poured into saturated aqueous sodium hydrogencarbonate, and the mixture was extracted with ethyl acetate. The organic layer was washed with water, and dried over anhydrous sodium sulfate, and then the solvent was evaporated. The residue was purified by silica gel column chromatography [eluted with hexane-ethyl acetate (19:1)] to obtain the title compound 8 (18.4 g, 78%) as colorless oil together with the recovered starting material (3.11 g, 17%).

IR (neat) $cm^{-1}$: 1747
$^1$H-NMR ($CDCl_3$) δ: 1.18 (9H, s), 1.35 (3H, d, J=7 Hz), 4.16 (1H, q, J=7 Hz), 5.13 (1H, d, J=12.5 Hz), 5.19 (1H, d, J=12.5 Hz), 7.29-7.42 (5H, m).

Example 7

Preparation of O-t-butyllactic acid dimer benzyl ester

[Formula 10]

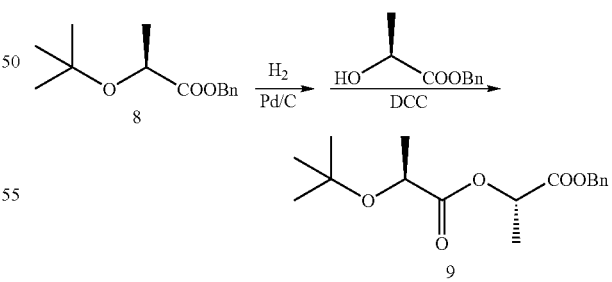

A suspension of the compound 8 (660 mg, 2.80 mmol) obtained above and palladium-carbon (10%, 42 mg) in methanol (12 ml) was subjected to catalytic reduction for 1 hour under a hydrogen atmosphere of atmospheric pressure. The reaction mixture was filtered through Cerite, and Cerite was washed with 10% methanol-chloroform. The solvent was evaporated to obtain 382 mg of a residue. A solution of this residue and benzyl lactate (471 mg, 2.62 mmol) in dichloromethane (8 ml) was added with dicyclohexylcarbodiimide (DCC, 664 mg, 3.22 mmol) and 4-dimethylaminopyridine (15 mg, 0.123 mmol), and the mixture was stirred at room temperature for 27 hours. The reaction mixture was cooled on an ice bath, and then added with ethyl alcohol (0.45 ml, 7.72 mmol) and acetic acid (0.12 ml, 2.10 mmol), and the mixture was stirred to decompose excessive DCC. The reaction mixture was added with saturated aqueous sodium hydrogencarbonate, and the mixture was filtered through Cerite, and extracted with ethyl acetate. The organic layer was washed with water, and dried over anhydrous sodium sulfate, then the solvent was evaporated, and the residue was purified by silica gel column chromatography [eluted with hexane-ethyl acetate (6:1)] to obtain the title compound 9 (688 mg, 80%) as colorless viscous oil.

IR (neat) cm$^{-1}$: 1747

$^1$H-NMR (CDCl$_3$) δ: 1.19 (9H, s), 1.35 (3H, d, J=7 Hz), 1.52 (3H, d, J=7 Hz), 4.18 (1H, q, J=7 Hz), 5.16 (2H, s), 5.19 (1H, q, J=7 Hz), 7.30-7.40 (5H, m).

Example 8

Preparation of O-t-butyllactic acid tetramer benzyl ester with saturated aqueous sodium hydrogencarbonate, and the mixture was extracted with ethyl acetate. The organic layer was dried over anhydrous sodium sulfate, and then the solvent was evaporated to obtain 67 mg of a residue 1. Separately, a suspension of the compound 9 (80 mg, 0.260 mmol) and palladium-carbon (10%, 5 mg) in methanol (3 ml) was subjected to catalytic reduction for 1 hour under a hydrogen atmosphere of atmospheric pressure. The resultant was treated in a conventional manner to obtain 60 mg of a residue 2. The residues 1 and 2 were combined, and dissolved in dichloromethane (2.5 ml), the solution was added with dicyclohexylcarbodiimide (60 mg, 0.291 mmol) and 4-dimethylaminopyridine (3 mg, 24.6 μmol), and the mixture was stirred at room temperature for 18 hours. The mixture was treated in a conventional manner, and then the residue was purified by silica gel column chromatography [eluted with hexane-ethyl acetate (5:1)] to obtain the title compound 10 (99 mg, 84%) as colorless viscous oil.

IR (neat) cm$^{-1}$: 1748, 1670

$^1$H-NMR (CDCl$_3$) δ: 1.21 (9H, s), 1.39 (3H, d, J=7 Hz), 1.517 (3H, d, J=7 Hz), 1.520 (3H, d, J=7 Hz), 1.57 (3H, d, J=7 Hz), 4.20 (1H, q, J=7 Hz), 5.10-5.23 (5H, m), 7.28-7.40 (5H, m)

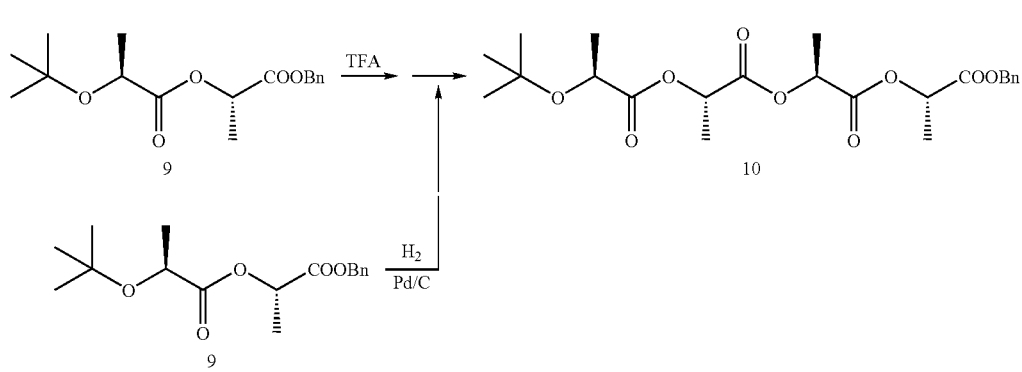

[Formula 11]

Example 9

Lactic Acid Tetramer Ester (Benzyl Ester) of Am-55s (5)

A solution of the compound 9 (80 mg, 0.260 mmol) obtained above in dichloromethane (0.8 ml) was cooled on ice, and added with trifluoroacetic acid (0.20 ml), and the mixture was stirred for 30 minutes, and further stirred at room temperature for 30 minutes. The reaction mixture was added

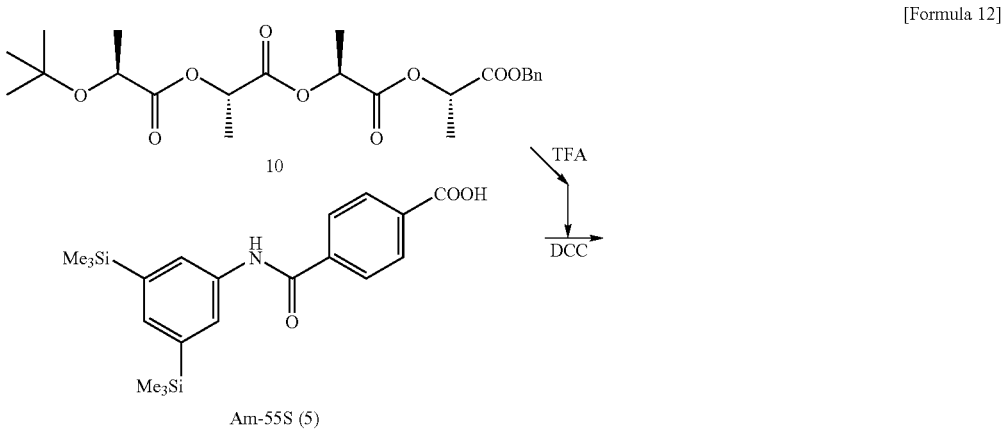

[Formula 12]

Am-55S (5)

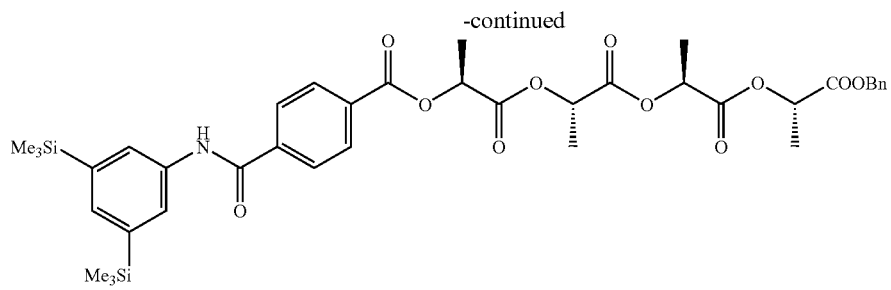

11

A solution of the compound 10 (84 mg, 0.186 mmol) obtained above in dichloromethane (0.8 ml) was cooled on ice, and added with trifluoroacetic acid (0.20 ml), and the mixture was stirred for 15 minutes, and further stirred at room temperature for 45 minutes. The reaction mixture was added with saturated aqueous sodium hydrogencarbonate, and the mixture was extracted with ethyl acetate. The organic layer was dried over anhydrous sodium sulfate, and then the solvent was evaporated to obtain 74 mg of a residue 1. A solution of this residue and the compound 5 (72 mg, 0.187 mmol) in dichloromethane (4 ml) was added with dicyclohexylcarbodiimide (46 mg, 0.223 mmol) and 4-dimethylaminopyridine (2 mg, 16.4 μmol), and the mixture was stirred at room temperature for 4 hours. The mixture was treated in a conventional manner, and then the residue was purified by silica gel column chromatography [eluted with benzene-ethyl acetate (14:1)] to obtain the title compound 11 (105 mg, 74%) as colorless viscous oil.

MS (m/z): 763 (M$^+$, 12), 512 (2), 440 (2), 368 (17), 176 (9), 104 (9), 91 (100), 73 (15), 56 (11)

IR (CHCl$_3$) cm$^{-1}$: 1748, 1672

$^1$H-NMR (CDCl$_3$) δ: 0.29 (18H, s), 1.50 (3H, d, J=7.5 Hz), 1.51 (3H, d, J=7 Hz), 1.59 (3H, d, J=7.5 Hz), 1.72 (3H, d, J=7 Hz), 5.08-5.24 (5H, m), 5.37 (1H, q, J=7 Hz), 7.28-7.39 (5H, m), 7.45 (1H, dif t, J=1 Hz), 7.80 (2H, br s), 7.92 (2H, A$_2$B$_2$, J=8.5 Hz), 8.12 (2H, A$_2$B$_2$, J=8.5 Hz), 8.22 (1H, br s, CONH)

Example 10

Lactic Acid Tetramer Ester (Carboxylic Acid) of Am-55s (5)

A suspension of the compound 11 (102 mg, 0.134 mmol) obtained above and palladium-carbon (10%, 10 mg) in methanol (5 ml) was subjected to catalytic reduction for 30 minutes under a hydrogen atmosphere of atmospheric pressure. The mixture was treated in a conventional manner, and then the residue was purified by silica gel column chromatography [eluted with chloroform to methanol-chloroform (19:1)] to obtain the title compound 12 (89 mg, 99%) as colorless foam.

MS (m/z): 673 (M$^+$, 69), 601 (42), 370 (79), 368 (71), 296 (45), 176 (88), 149 (62), 104 (65), 73 (100), 55 (58), 45 (49)

IR (KBr) cm$^{-1}$: 1753, 1726, 1652

$^1$H-NMR (CDCl$_3$) δ: 0.31 (18H, s), 1.56 (3H, d, J=7 Hz), 1.57 (3H, d, J=7.5 Hz), 1.62 (3H, d, J=7 Hz), 1.73 (3H, d, J=7.5 Hz), 5.12-5.28 (3H, m), 5.40 (1H, q, J=7 Hz), 7.46 (1H, br s), 7.76 (2H, br s), 7.87 (1H, br s, CONH), 7.95 (2H, A$_2$B$_2$, J=8 Hz), 8.19 (2H, A$_2$B$_2$, J=8 Hz)

Example 11

N-Ethoxycarbonylated Compound (14) of Am-81 (13)

[Formula 14]

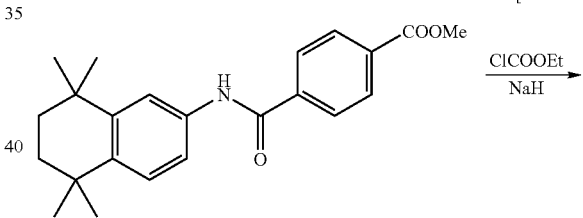

Am-81 (13)

[Formula 13]

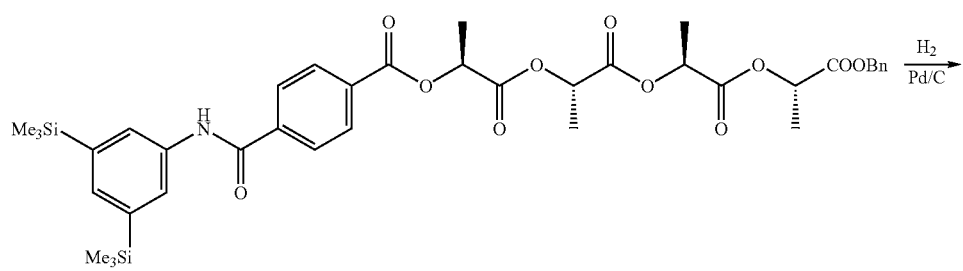

11

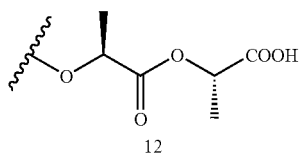

12

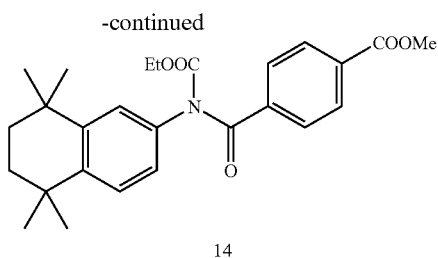

14

A solution of Am-81 (13, 110 mg, 0.301 mmol) in DMF (3 ml) was cooled on ice, and added with sodium hydride (60%, 30 mg, 0.750 mmol), and the mixture was stirred for 10 minutes. The mixture was added with ethyl chloroformate (72 μl, 0.753 mmol), and the mixture was further stirred for 2 hours under ice cooling. The mixture was added with saturated aqueous ammonium chloride, and the mixture was extracted with ethyl acetate. The organic layer was washed with water, and dried over anhydrous sodium sulfate, and then the solvent was evaporated. The residue was purified by silica gel column chromatography [eluted with benzene-ethyl acetate (119:1)], and recrystallized to obtain the title compound 14 (96 mg, 73%) together with the recovered compound 13 (23 mg, 21%).

Compound 14: colorless fine needles, melting point: 131-132° C. (dichloromethane-hexane).

MS (m/z): 437 (M$^+$, 17), 422 (10), 350 (7), 229 (10), 214 (72), 163 (100), 135 (19), 103 (13), 43 (11), 29 (16)

IR (KBr) cm$^{-1}$: 1736, 1722, 1687

$^1$H-NMR (CDCl$_3$) δ: 1.04 (3H, t, J=7 Hz), 1.23 (6H, s), 1.28 (6H, s), 1.68 (4H, s), 3.94 (3H, s), 4.12 (2H, q, J=7 Hz), 6.98 (1H, dd, J=8, 2.5 Hz), 7.09 (1H, d, J=2.5 Hz), 7.33 (1H, d, J=8 Hz), 7.72 (2H, A$_2$B$_2$, J=8 Hz), 8.08 (2H, A$_2$B$_2$, J=8 Hz)

Example 12

N-Ethoxycarbonylated Compound (16) of Am-580 Ethyl Ester (15)

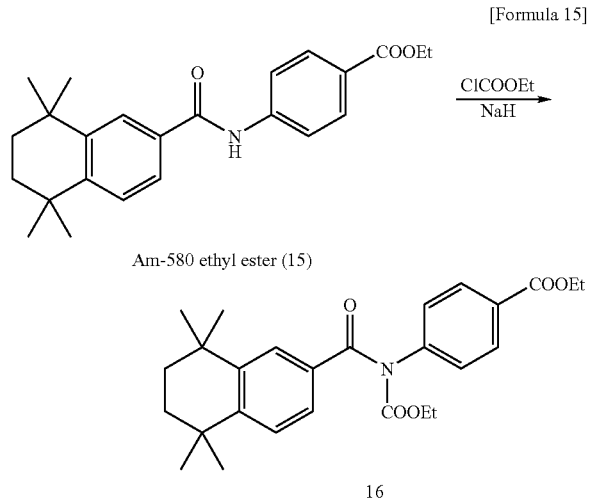

In the same manner as that of the preparation of the compound 14 mentioned above, 169 mg of a reaction mixture was obtained from the compound 15 (120 mg, 0.317 mmol). This was dissolved in ethyl alcohol (3 ml), the solution was stirred for 1.5 hours with heating at 50° C., and then the solvent was evaporated. The residue was purified by silica gel column chromatography [eluted with benzene-ethyl acetate (79:1)], and recrystallized to obtain the title compound 16 (120 mg, 84%) together with the recovered compound 15 (12 mg, 10%).

Compound 16: colorless prisms, melting point: 125-126° C. (dichloromethane-hexane)

MS (m/z): 451 (M$^+$, 1), 406 (1), 215 (100), 172 (4), 157 (5), 43 (4)

IR (KBr) cm$^{-1}$: 1737, 1708, 1688

$^1$H-NMR (CDCl$_3$) δ: 1.02 (3H, t, J=7 Hz), 1.25 (6H, s), 1.28 (6H, s), 1.38 (3H, t, J=7 Hz), 1.68 (4H, s), 4.13 (2H, q, J=7 Hz), 4.37 (2H, q, J=7 Hz), 7.31 (2H, A$_2$B$_2$, J=8 Hz), 7.35 (1H, d, J=8 Hz), 7.49 (1H, dd, J=8, 2 Hz), 7.67 (1H, d, J=2 Hz), 8.08 (2H, A$_2$B$_2$, J=8 Hz)

Example 13

Propionic Acid Ester Analogue (18) of Am-580

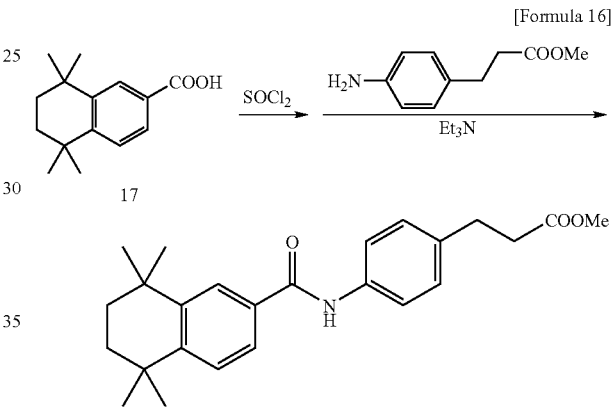

A solution of the compound 17 (39 mg, 0.168 mmol) in benzene (2.5 ml) was added with thionyl chloride (122 μl, 1.67 mmol) and DMF (1 drop), and the mixture was refluxed by heating for 1 hour. Volatile substances were evaporated, then the residue was added with benzene (3 ml), the solvent was evaporated again, and the residue was dried under reduced pressure. A solution of this residue in dichloromethane (1 ml) was cooled on ice, and added with a solution of methyl 3-(4-aminophenyl)propionate (36 mg, 0.201 mmol) and triethylamine (117 μl, 0.841 mmol) in dichloromethane (2 ml), and the mixture was stirred at 0° C. for 30 minutes, and at room temperature for further 16 hours. The reaction mixture was added with saturated aqueous sodium hydrogencarbonate, and extracted with ethyl acetate. The organic layer was washed with water, and dried over anhydrous sodium sulfate, and then the solvent was evaporated. The residue was purified by silica gel column chromatography (eluted with chloroform), and the residue was recrystallized to obtain the title compound 18 (55 mg, 83%) together with the recovered compound 17 (6 mg, 15%).

Compound 18: colorless needles, melting point: 118.5-119.5° C. (dichloromethane-hexane)

MS (m/z): 393 (M$^+$, 15), 249 (4), 215 (100), 172 (5), 157 (10), 91 (6), 43 (9)

IR (KBr) cm$^{-1}$: 1731, 1638

$^1$H-NMR (CDCl$_3$) δ: 1.29 (6H, s), 1.30 (6H, s), 1.70 (4H, s), 2.61 (2H, t, J=8 Hz), 2.92 (2H, t, J=8 Hz), 3.66 (3H, s), 7.17

(2H, A$_2$B$_2$, J=8.5 Hz), 7.36 (1H, d, J=8 Hz), 7.55 (1H, dd, J=8, 2 Hz), 7.56 (2H, A$_2$B$_2$, J=8.5 Hz), 7.86 (1H, d, J=2 Hz), 7.99 (1H, br s, CONH)

Example 14

Propionic Acid Analogue (19) of Am-580

[Formula 17]

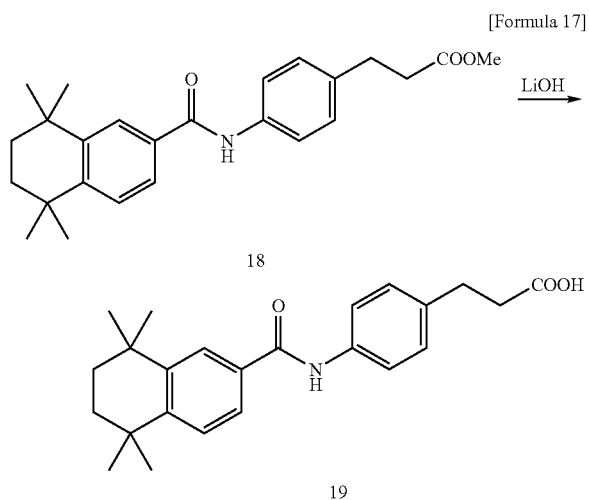

The compound 18 (30 mg, 76.3 μmol) obtained above was dissolved in methanol-1,2-dimethoxyethane-water (3:2:1, 3 ml), the solution was added with lithium hydroxide monohydrate (6.5 mg, 0.155 mmol), and the mixture was refluxed by heating for 1 hour. The reaction solution was cooled on ice, and then added with aqueous hydrochloric acid (1 N, 155 μl, 0.155 mmol), and the mixture was extracted with ethyl acetate. The organic layer was washed with water, and dried over anhydrous sodium sulfate, and then the solvent was evaporated. The residue was recrystallized to obtain the title compound 19 (28 mg, 97%).

Colorless prisms, melting point: 172.5-174° C. (dichloromethane-hexane)

MS (m/z): 379 (M$^+$, 15), 215 (100), 157 (12), 131 (5), 128 (6), 91 (5), 43 (12)

IR (KBr) cm$^{-1}$: 1704, 1638

$^1$H-NMR (CDCl$_3$) δ: 1.30 (6H, s), 1.32 (6H, s), 1.71 (4H, s), 2.68 (2H, t, J=8 Hz), 2.96 (2H, t, J=8 Hz), 7.22 (2H, A$_2$B$_2$, J=8.5 Hz), 7.39 (1H, d, J=8 Hz), 7.54 (1H, dd, J=8, 2 Hz), 7.57 (2H, A$_2$B$_2$, J=8.5 Hz), 7.75 (1H, br s, CONH), 7.85 (1H, d, J=2 Hz)

Example 15

Propionic Acid Ester Analogue (21) of Am-80

[Formula 18]

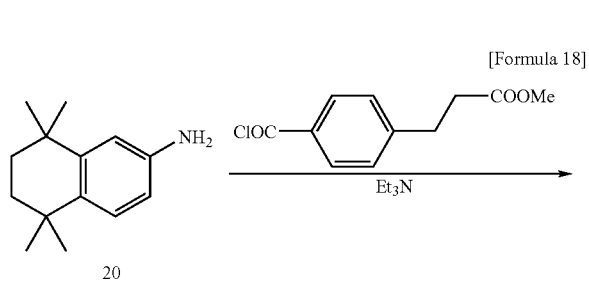

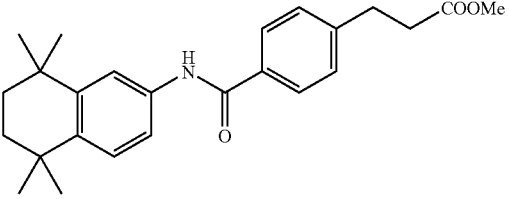

A solution of 4-[2-(methoxycarbonyl)ethyl]benzoic acid (77 mg, 0.370 mmol) and thionyl chloride (135 μl, 1.85 mmol) in benzene (3 ml) was refluxed by heating for 1 hour. The resultant was treated in the same manner as that of Example 13 to obtain an acid chloride. This acid chloride was dissolved in dichloromethane (1 ml), this solution was added dropwise with a solution of the compound 20 (50 mg, 0.246 mmol) and triethylamine (171 μl, 1.23 mmol) in dichloromethane (1 ml) under ice cooling, and the mixture was stirred for 10 minutes, and further stirred at room temperature for 4 hours. The reaction mixture was added with saturated aqueous sodium hydrogencarbonate, and the mixture was extracted with ethyl acetate. The organic layer was washed with water, and dried over anhydrous sodium sulfate, and then the solvent was evaporated. The residue was purified by silica gel column chromatography [eluted with benzene-ethyl acetate (8:1)], and recrystallized to obtain the title compound 21 (94 mg, 97%).

Compound 21: colorless prisms, melting point: 135-136° C. (dichloromethane-hexane)

MS (m/z): 393 (M$^+$, 35), 378 (100), 362 (5), 191 (76), 131 (35), 103 (18), 91 (10), 59 (7), 43 (10)

IR (KBr) cm$^{-1}$: 1707, 1659

$^1$H-NMR (CDCl$_3$) δ: 1.28 (6H, s), 1.30 (6H, s), 1.69 (4H, s), 2.67 (2H, t, J=7.5 Hz), 3.02 (2H, t, J=7.5 Hz), 3.68 (3H, s), 7.30 (1H, d, J=8.5 Hz), 7.32 (2H, A$_2$B$_2$, J=8 Hz), 7.41 (1H, dd, J=8.5, 2.5 Hz), 7.53 (1H, d, J=2.5 Hz), 7.69 (1H, br s, CONH), 7.80 (2H, A$_2$B$_2$, J=8 Hz)

Example 16

Propionic Acid Analogue (22) of Am-80

[Formula 19]

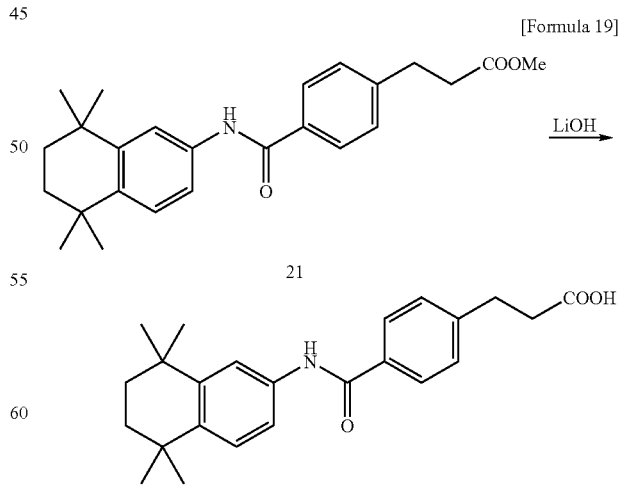

In the same manner as that of Example 14, the compound 21 (50 mg, 0.127 mmol) was hydrolyzed with lithium hydroxide, the resultant was subjected to a post-treatment, and the residue was recrystallized to obtain the title compound 22 (45 mg, 93%).

Colorless needles, melting point: 229-230° C. (methanol-dichloromethane)

MS (m/z): 379 (M+, 33), 364 (100), 177 (92), 131 (14), 107 (22), 103 (20), 77 (16)

IR (KBr) cm$^{-1}$: 1711, 1616

$^1$H-NMR (CDCl$_3$) δ: 1.28 (6H, s), 1.30 (6H, s), 1.69 (4H, s), 2.72 (2H, t, Hz), 3.04 (2H, t, J=7.5 Hz), 7.30 (1H, d, J=8.5 Hz), 7.33 (2H, A$_2$B$_2$, J=8.5 Hz), 7.41 (1H, dd, J=8.5, 2 Hz), 7.53 (1H, d, J=2 Hz), 7.73 (1H, br s, CONH), 7.80 (2H, A$_2$B$_2$, J=8.5 Hz)

Example 17

Condensation of Am-80 and Alanine Methyl Ester

[Formula 20]

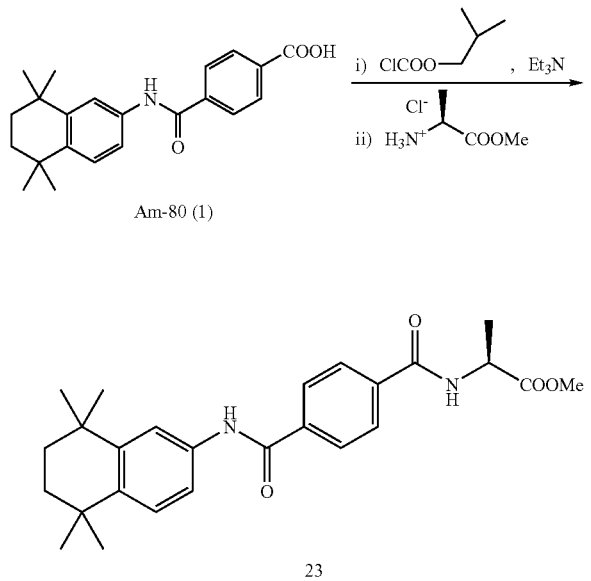

An ice-cooled solution of Am-80 (1, 60 mg, 0.171 mmol) and triethylamine (95 μl, 0.683 mmol) in dichloromethane (3 ml) was added with isobutyl chloroformate (24 μl, 0.185 mmol), and the mixture was stirred for 1 hour. This reaction mixture was added with L-alanine methyl ester hydrochloride (29 mg, 0.208 mmol), and the mixture was further stirred at room temperature for 16 hours. The reaction mixture was added with saturated aqueous sodium hydrogencarbonate, and the mixture was extracted with ethyl acetate. The organic layer was washed with water, and dried over anhydrous sodium sulfate, and then the solvent was evaporated. The residue was purified by silica gel column chromatography (eluted with 5 to 10% methanol-chloroform) to obtain the title compound 23 (64 mg, 86%) together with the recovered compound 1 (6.5 mg, 11%).

Compound 23: colorless candy-like substance

MS (m/z): 436 (M+, 58), 421 (84), 334 (17), 318 (100), 234 (26), 174 (23), 104 (62), 76 (25), 43 (34)

IR (CHCl$_3$) cm$^{-1}$: 1733, 1657

$^1$H-NMR (CDCl$_3$) δ: 1.27 (12H, s), 1.50 (3H, d, J=7 Hz), 1.68 (4H, s), 3.75 (3H, s), 4.74 (1H, dq, J=7.5, 7 Hz), 7.22 (1H, br d, J=7.5 Hz, NH), 7.27 (1H, d, J=8.5 Hz), 7.51 (1H, dd, J=8.5, 2 Hz), 7.65 (2H, A$_2$B$_2$, J=8.5 Hz), ca. 7.64-7.67 (1H, m), 7.73 (2H, A$_2$B$_2$, J=8.5 Hz), 8.69 (1H, br s, CONH)

Example 18

Hydrolysis of Condensate of Am-80 and Alanine Methyl Ester

[Formula 21]

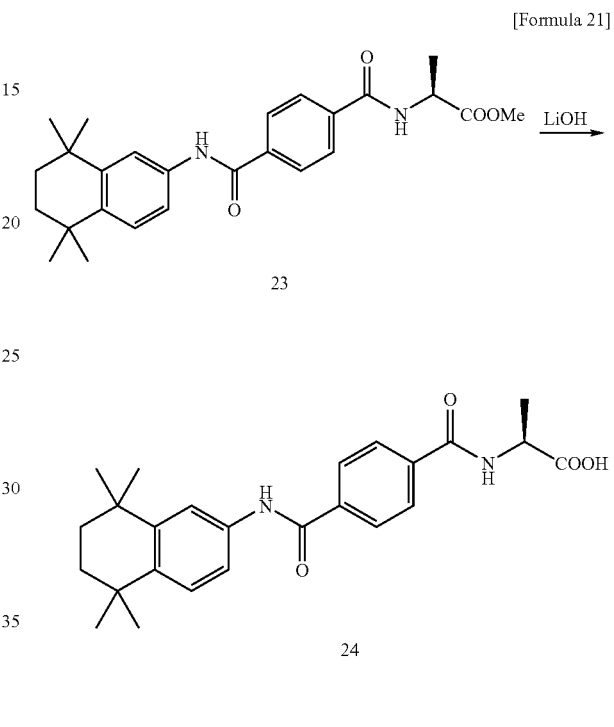

In the same manner as that of Example 14, the compound 23 (61 mg, 0.140 mmol) obtained above was dissolved in methanol-1,2-dimethoxyethane-water (3:2:1, 3 ml), the solution was added with lithium hydroxide monohydrate (7 mg, 0.167 mmol), and the mixture was refluxed by heating for 1 hour. The reaction solution was cooled with ice, and then added with aqueous hydrochloric acid (1 N, 167 μl, 0.167 mmol), and the mixture was extracted with ethyl acetate. The organic layer was washed with water, and dried over anhydrous sodium sulfate, and then the solvent was evaporated. The residue was recrystallized to obtain the title compound 24 (51 mg, 86%).

Colorless prisms, melting point: 197-198° C. (dichloromethane-ethyl acetate)

MS (m/z): 422 (M+, 57), 407 (89), 318 (100), 220 (34), 174 (30), 104 (73), 76 (36), 43 (45)

IR (KBr) cm$^{-1}$: 1720, 1660, 1624

$^1$H-NMR (DMSO-d6) δ: 1.23 (6H, s), 1.24 (6H, s), 1.41 (3H, d, J=7 Hz), 1.64 (4H, s), 4.43 (1H, dq, J=7, 7 Hz), 7.28 (1H, d, J=8.5 Hz), 7.57 (1H, dd, J=8.5, 2 Hz), 7.67 (1H, d, J=2 Hz), 7.99 (2H, A$_2$B$_2$, J=8.5 Hz), 8.04 (2H, A$_2$B$_2$, J=8.5 Hz), 8.81 (1H, d, J=7 Hz, NH), 10.19 (1H, br s, CONH)

Example 19

Condensation of Am-80 and Glycidylglycine Methyl Ester

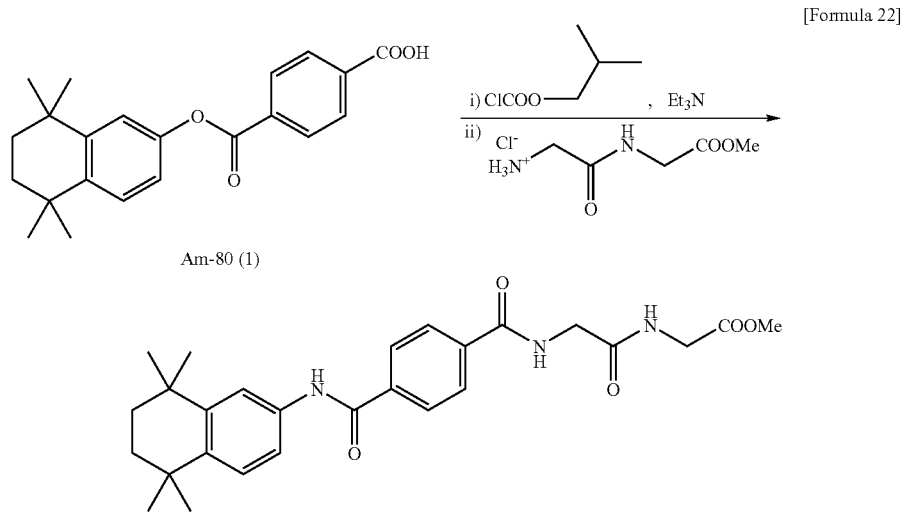

[Formula 22]

In the same manner as that of Example 17, Am-80 (1, 60 mg, 0.171 mmol) was condensed with glycidylglycine methyl ester hydrochloride (38 mg, 0.208 mmol). The resultant was subjected to a post-treatment, and then the residue was purified by silica gel column chromatography (eluted with 5 to 10% methanol-chloroform) to obtain the title compound 25 (58 mg, 71%) together with the recovered compound 1 (9 mg, 15%).

Compound 25: colorless needles, melting point: 240-242° C. (methanol-dichloromethane)

MS (m/z): 479 (M$^+$, 92), 464 (48), 375 (56), 334 (30), 318 (100), 291 (26), 160 (67), 104 (89), 88 (42)

IR (KBr) cm$^{-1}$: 1745, 1655, 1637

$^1$H-NMR (DMSO-d6) δ: 1.23 (6H, s), 1.24 (6H, s), 1.64 (4H, s), 3.62 (3H, s), 3.87 (2H, d, J=6 Hz), 3.94 (2H, d, J=6 Hz), 7.28 (1H, d, J=8.5 Hz), 7.57 (1H, dd, J=8.5, 2 Hz), 7.67 (1H, d, J=2 Hz), 8.00 (2H, A$_2$B$_2$, J=9 Hz), 8.04 (2H, A$_2$B$_2$, J=9 Hz), 8.38 (1H, t, J=6 Hz, NH), 8.95 (1H, t, J=6 Hz, NH), 10.19 (1H, br s, CONH)

Example 20

Hydrolysis of Condensate of Am-80 and Glycidylglycine Methyl Ester

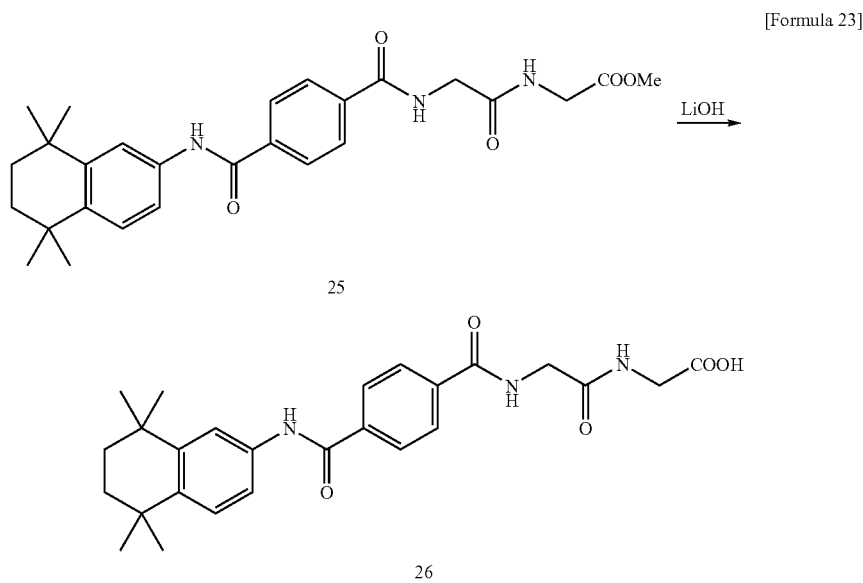

[Formula 23]

In the same manner as that of Example 18, the compound 25 (50 mg, 0.104 mmol) obtained above was hydrolyzed with lithium hydroxide monohydrate (6 mg, 0.143 mmol) under reflux by heating. The resultant was treated in a conventional manner, and then the residue was recrystallized to obtain the title compound 26 (44 mg, 91%).

Colorless prisms, melting point: 228-229° C. (methanol-ethyl acetate)

MS (m/z): 465 (M$^+$, 15), 432 (18), 408 (47), 393 (83), 375 (83), 347 (34), 336 (63), 318 (90), 206 (44), 160 (100), 149 (49), 104 (100), 76 (51), 43 (47)

IR (KBr) cm$^{-1}$: 1715, 1664, 1634

$^1$H-NMR (DMSO-d6) δ: 1.23 (6H, s), 1.24 (6H, s), 1.64 (4H, s), 3.76 (2H, d, J=6 Hz), 3.94 (2H, d, J=6 Hz), 7.28 (1H, d, J=8.5 Hz), 7.57 (1H, dd, J=8.5, 2 Hz), 7.67 (1H, d, J=2 Hz), 8.00 (2H, $A_2B_2$, J=8.5 Hz), 8.04 (2H, $A_2B_2$, J=8.5 Hz), 8.23 (1H, t, J=6 Hz, NH), 8.93 (1H, t, J=6 Hz, NH), 10.19 (1H, br s, CONH)

Example 21

N-(4-Methoxycarbonyl)-benzoylated compound (27) of Am-81 (13)

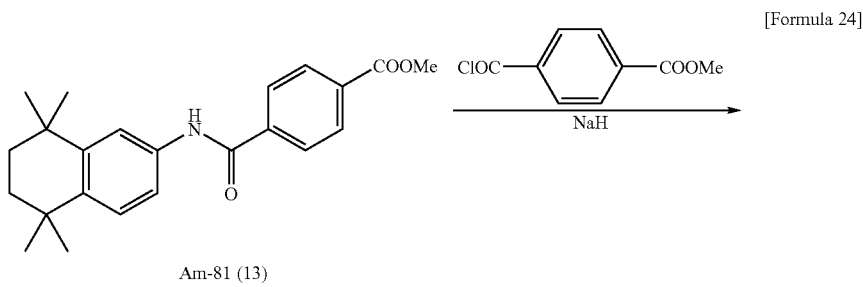

In the same manner as that of Example 11, Am-81 (13, 100 mg, 0.274 mmol) was treated with sodium hydride (60%, 22 mg, 0.550 mmol) and terephthalic acid monomethyl chloride (71 mg, 0.358 mmol) in DMF (3 ml) under ice cooling. The reaction product was purified by silica gel column chromatography [eluted with hexane-ethyl acetate (6:1)] to obtain the title compound 27 (71 mg, 49%) together with the recovered compound 13 (22 mg, 22%).

MS (m/z): 527 (M$^+$, 13), 512 (4), 163 (100), 135 (14), 103 (10), 77 (5)

IR (KBr) cm$^{-1}$: 1720, 1696, 1668

$^1$H-NMR (CDCl$_3$) δ: 1.05 (6H, s), 1.23 (6H, s), 1.61 (4H, s), 3.92 (6H, s), 6.91 (1H, d, J=2 Hz), 6.96 (1H, dd, J=8.5, 2 Hz), 7.29 (1H, d, J=8.5 Hz), 7.75 (4H, $A_2B_2$, J=0.8 Hz), 8.01 (41-1, $A_2B_2$, J=8 Hz)

Example 22

4-(3,5-Bistrimethylsilanylbenzolyamino)phenylpropionic acid

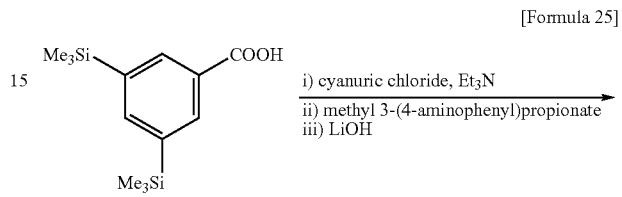

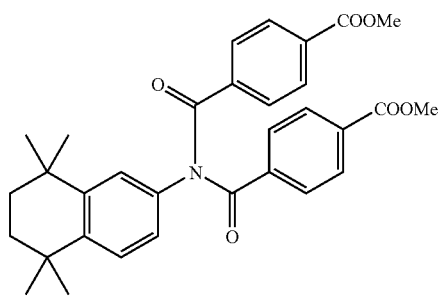

A solution of 3,5-bis(trimethylsilyl)benzoic acid (120 mg, 0.451 mmol) and cyanuric chloride (125 mg, 0.678 mmol) in acetone (4 ml) was cooled on ice, and added with triethylamine (251 μl, 1.80 mmol), and the mixture was stirred for 5 minutes. The mixture was further stirred at room temperature for 3.5 hours, and then added with methyl 3-(4-aminophenyl)propionate (121 mg, 0.676 mmol), and the mixture was further stirred for 16 hours. The reaction mixture was added with saturated aqueous sodium hydrogencarbonate, the mixture was extracted with ethyl acetate, the organic layer was treated in a conventional manner, and then the residue was separated by silica gel chromatography [eluted with benzene-ethyl acetate (14:1)], and recrystallized to obtain methyl 4-(3,5-bistrimethylsilanylbenzolyamino)phenylpropionate (169 mg, 88%) as colorless scales.

Mp: 119-120.5° C. and 136-137° C. (dichloromethane-hexane)

MS (m/z): 427 ($M^+$, 25), 249 (100), 221 (9), 73 (64)

IR (KBr) $cm^{-1}$: 1733, 1643, 1600

$^1$H-NMR (CDCl$_3$) δ: 0.32 (18H, s), 2.64 (2H, t, J=8 Hz), 2.95 (2H, t, J=8 Hz), 3.68 (3H, s), 7.22 (2H, A$_2$B$_2$, J=8.5 Hz), 7.58 (2H, A$_2$B$_2$, J=8.5 Hz), 7.72 (1H, br s, NH), 7.82 (1H, dd, J=1, 1 Hz), 7.93 (2H, d, J=1 Hz)

The above methyl ester (556 mg, 1.30 mmol) was dissolved in methanol-DME-water (3:2:1, 9 ml), the solution was added with lithium hydroxide monohydrate (LiOH.H$_2$O, 82 mg, 1.95 mmol), and the mixture was refluxed by heating for 2 hours. The reaction mixture was cooled on ice, and then added with aqueous hydrochloric acid (1 N, 2.00 ml, 2.00 mmol), and the mixture was extracted with ethyl acetate. The organic layer was washed with water, and dried over anhydrous sodium sulfate, then the solvent was evaporated, and the residue was recrystallized to obtain the title compound (522 mg, 97%) as colorless prisms.

Mp: 151-152° C. (dichloromethane-hexane)

MS (m/z): 413 ($M^+$, 22), 398 (3), 249 (100), 221 (9), 133 (7), 83 (9), 73 (71)

IR (KBr) cm-1: 1706, 1639

$^1$H-NMR (CDCl$_3$) δ: 0.31 (18H, s), 2.69 (2H, t, J=7.5 Hz), 2.97 (2H, t, J=7.5 Hz), 7.23 (2H, A$_2$B$_2$, J=8.5 Hz), 7.59 (2H, A$_2$B$_2$, J=8.5 Hz), 7.78 (1H, br s, NH), 7.81 (1H, dd, J=1, 1 Hz), 7.93 (2H, d, J=1 Hz)

Example 23

4-Formyl-N-(5,6,7,8-tetrahydro-5,5,8,8-tetramethyl-2-naphthyl)benzamide was filtered through Cerite, and then washed with tetrahydrofuran (3 ml). The filtrate was cooled on ice, and added with NaBH$_4$ (208 mg, 5.47 mmol), then the mixture was slowly added dropwise with water (4 ml) with vigorous stirring, and stirring was further continued over 18 hours until the reaction mixture became 26° C. The reaction mixture was added with saturated aqueous ammonium chloride, the mixture was extracted with ethyl acetate, and the organic layer was treated in a conventional manner. The residue was separated by silica gel chromatography [eluted with hexane-ethyl acetate (2:1)], and recrystallized to obtain 4-hydroxymethyl-N-(5,6,7,8-tetrahydro-5,5,8,8-tetramethyl-2-naphthyl)benzamide (290 mg, 94%) as colorless prisms.

Mp: 161-162.5° C. (dichloromethane-hexane)

MS (m/z): 337 ($M^+$, 27), 322 (87), 135 (100), 107 (18), 89 (34), 77 (28)

IR (KBr) $cm^{-1}$: 1634

$^1$H-NMR (CDCl$_3$) δ: 1.28 (6H, s), 1.30 (6H, s), 1.69 (4H, s), 1.93 (1H, t, J=4.5 Hz, OH), 4.78 (2H, d, J=4.5 Hz), 7.30 (1H, d, J=8.5 Hz), 7.43 (1H, dd, J=8.5, 2.5 Hz), 7.47 (2H, A$_2$B$_2$, J=8 Hz), 7.54 (1H, d, J=2.5 Hz), 7.76 (1H, br s, NH), 7.85 (2H, A$_2$B$_2$, J=8 Hz)

A solution of the above alcohol (1.891 g, 5.61 mmol) in dichloromethane (35 ml) was added with manganese dioxide (3.905 g, 44.9 mmol), and the mixture was refluxed by heating for 2 hours with stirring. The reaction mixture was filtered through Cerite under reduced pressure, and Cerite was washed with chloroform. The solvent was evaporated, and then the residue was recrystallized to obtain the title compound (1.802 g, 96%) as colorless prisms.

Mp: 185.5-186.5° C. (dichloromethane-hexane)

MS (m/z): 335 ($M^+$, 32), 320 (100), 133 (68), 105 (28), 77 (24), 51 (9)

IR (KBr) $cm^{-1}$: 1690, 1662

$^1$H-NMR (CDCl$_3$) δ: 1.29 (6H, s), 1.30 (6H, s), 1.70 (4H, s), 7.33 (1H, d, J=8.5 Hz), 7.44 (1H, dd, J=8.5, 2 Hz), 7.53 (1H, d, J=2 Hz), 7.79 (1H, br s, NH), 7.99 (2H, A$_2$B$_2$, J=8.5 Hz), 8.03 (2H, A$_2$B$_2$, J=8.5 Hz)

Example 24

4-[(5,6,7,8-Tetrahydro-5,5,8,8-tetramethyl-2-naphthyl)carbamoyl]cinnamic acid

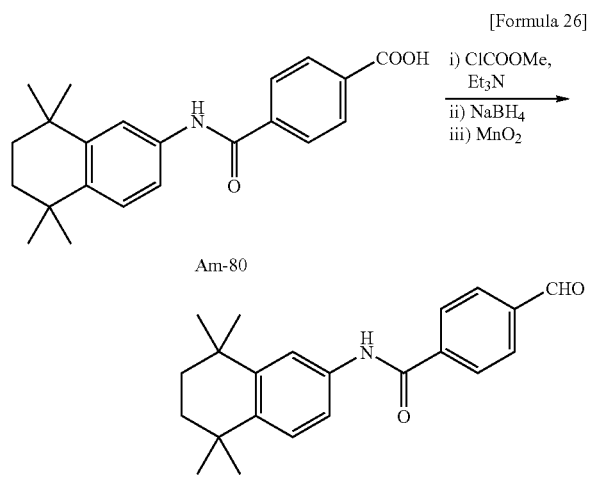

[Formula 26]

Am-80

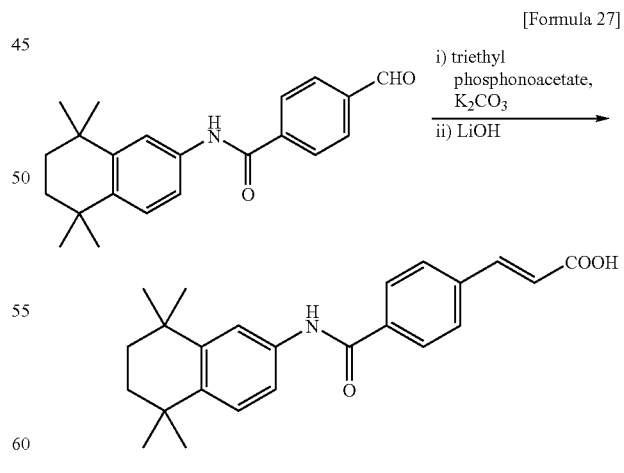

[Formula 27]

A solution of Am-80 (320 mg, 0.912 mmol) and triethylamine (152 μl, 1.09 mmol) in tetrahydrofuran (5 ml) was cooled to −20° C., and added dropwise with a solution of methyl chloroformate (82 μl, 1.06 mmol) in tetrahydrofuran, and the mixture was stirred for 1 hour. The reaction mixture A solution of 4-formyl-N-(5,6,7,8-tetrahydro-5,5,8,8-tetramethyl-2-naphthyl)benzamide (1.765 g, 5.27 mmol) and triethyl phosphonoacetate (1.523 g, 6.80 mmol) in ethanol (40 ml) was added with potassium carbonate (910 mg, 6.59 mmol), and the mixture was stirred at 62 to 64° C. for 3 hours. The reaction mixture was cooled on ice, and then added with saturated aqueous ammonium chloride, and the mixture was extracted with ethyl acetate. The organic layer was treated in a conventional manner, and then residue was separated by silica gel chromatography [eluted with benzene-ethyl acetate (39:1 to 14:1)], and recrystallized to obtain ethyl 4-[(5,6,7,8-tetrahydro-5,5,8,8-tetramethyl-2-naphthyl)carbamoyl]cinnamate (2.076 g, 97%) as colorless needles.

Mp: 166-166.5° C. (dichloromethane-hexane)

MS (m/z): 405 ($M^+$, 31), 390 (100), 203 (60), 175 (22), 102 (29), 91 (20)

IR (KBr) $cm^{-1}$: 1697, 1663, 1644

$^1$H-NMR (CDCl$_3$) δ: 1.28 (6H, s), 1.30 (6H, s), 1.35 (3H, t, J=7 Hz), 1.70 (4H, s), 4.29 (2H, q, J=7 Hz), 6.52 (1H, d, J=16 Hz), 7.31 (1H, d, J=8.5 Hz), 7.43 (1H, dd, J=8.5, 2.5 Hz), 7.53 (1H, d, J=2.5 Hz), 7.63 (2H, A$_2$B$_2$, J=8 Hz), 7.71 (1H, d, J=16 Hz), 7.74 (1H, br s, NH), 7.89 (2H, A$_2$B$_2$, J=8 Hz)

The above ester (109 mg, 0.269 mmol) was dissolved in methanol-DME-water (3:2:1, 4.2 ml), the solution was added with lithium hydroxide monohydrate (LiOH.H$_2$O, 15 mg, 0.357 mmol), and the mixture was refluxed by heating for 1 hour. The mixture was cooled on ice, and then added with aqueous hydrochloric acid (1 N, 0.36 ml, 0.36 mmol), and the mixture was extracted with ethyl acetate. The organic layer was washed with water, and dried over anhydrous sodium sulfate, and then the solvent was evaporated. The residue was recrystallized to obtain the title compound (96 mg, 95%) as colorless prisms.

Mp: 226-227° C. (dichloromethane)

MS (m/z): 377 ($M^+$, 29), 362 (100), 175 (96), 147 (18), 102 (17), 91 (41), 44 (32)

IR (KBr) $cm^{-1}$: 1682, 1646, 1625

$^1$H-NMR (CDCl$_3$) δ: 1.29 (6H, s), 1.31 (6H, s), 1.70 (4H, s), 6.54 (1H, d, J=16 Hz), 7.32 (1H, d, J=8.5 Hz), 7.43 (1H, dd, J=8.5, 2.5 Hz), 7.53 (1H, d, J=2.5 Hz), 7.66 (2H, A$_2$B$_2$, J=8 Hz), 7.74 (1H, br s, NH), 7.81 (1H, d, J=16 Hz), 7.91 (2H, A$_2$B$_2$, J=8 Hz)

INDUSTRIAL APPLICABILITY

Since the compounds of the present invention have a property that they are converted into a retinoid after they are absorbed by living bodies, they are useful as a retinoid prodrug compound.

What is claimed is:

1. A compound or salt thereof represented by the following formula (I):

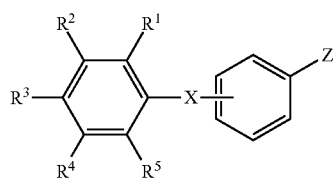

wherein:
(a) $R^1$, $R^4$ and $R^5$ are hydrogen atoms, and $R^2$ and $R^3$ are bond to each other to form a 5,5,8,8-tetramethyl-5,6,7,8-tetrahydronaphthalene ring together with the benzene ring to which $R^2$ and $R^3$ are bound, or
(b) $R^1$, $R^3$ and $R^5$ are hydrogen atoms, and $R^2$ and $R^4$ are trimethylsilyl groups;
X represents —NH—CO— or —CO—NH; and
Z represents —CH$_2$—COOH or —CH$_2$—CH$_2$—COOH; and
wherein X and Z are at para positions with respect to each other on the benzene ring to which X and Z are bound.

2. The compound or salt thereof according to claim 1, wherein $R^1$, $R^4$ and $R^5$ are hydrogen atoms, and $R^2$ and $R^3$ are bond to each other to form a 5,5,8,8-tetramethyl-5,6,7,8-tetrahydronaphthalene ring together with the benzene ring to which $R^2$ and $R^3$ are bound.

3. The compound or salt thereof according to claim 1, wherein $R^1$, $R^3$ and $R^5$ are hydrogen atoms, and $R^2$ and $R^4$ are trimethylsilyl groups.

4. The compound or salt thereof according to claim 1, wherein X represents —NH—CO—.

5. The compound or salt thereof according to claim 4, wherein Z represents —CH$_2$—CH$_2$—COOH.

6. The compound or salt thereof according to claim 4, wherein Z represents —CH$_2$—COOH.

7. The compound or salt thereof according to claim 1, wherein X represents —CO—NH.

* * * * *